United States Patent [19]
Berg et al.

[11] Patent Number: 5,661,002
[45] Date of Patent: *Aug. 26, 1997

[54] MODIFIED TRANSCRIPTION CONTROL UNIT AND USES THEREOF

[75] Inventors: David T. Berg, Beech Grove; Brian W. Grinnell, Indianapolis, both of Ind.

[73] Assignee: Eli Lilly and Company, Indianapolis, Ind.

[*] Notice: The term of this patent shall not extend beyond the expiration date of Pat. No. 5,270,178.

[21] Appl. No.: 446,126

[22] Filed: May 19, 1995

Related U.S. Application Data

[62] Division of Ser. No. 160,450, Dec. 1, 1993, Pat. No. 5,573,938, which is a continuation of Ser. No. 484,082, Feb. 23, 1990, abandoned.

[51] Int. Cl.$^6$ ...................................................... C12P 21/00
[52] U.S. Cl. ........................................ 435/69.1; 435/70.1
[58] Field of Search .................................. 435/69.1, 70.1, 435/172.3, 320.1; 536/23.1, 24.1; 935/22, 23, 34, 36

[56] References Cited

U.S. PATENT DOCUMENTS 5,270,178  12/1993  Gerlitz et al. ............................ 435/69.1

FOREIGN PATENT DOCUMENTS 0245949  11/1987  European Pat. Off. ......... C12N 15/00

OTHER PUBLICATIONS

Grinnell, et al, 1987, BioTechnology 5:1189–1192.
Grinnell, et al, 1986, Mol. Cell. Biol. 6:3596–3605.
Berg, et al, 1988, Nuc. Acids Res., 16:9057.
Grinnell, et al, 1988, Mol. Cell. Biol. 8:3488.
Berg, et al, 1989, Mol. Cell. Biol. 9:5248–5253.
Zhang, et al, 1989, J. Biol. Chem. 264: 10679.
Randal J. Kaufman, 1985, Proc. Natl. Acad. Sci. USA, 82, 689–693.
Logan, et al, 1984, Proc. Natl. Acad. Sci. USA, 81, 3655–3659.
Alonso–Caplen, et al, 1988 Journal of Virology, 62(5) 1606–1616.

*Primary Examiner*—David Guzo
*Assistant Examiner*—Robert Schwartzman
*Attorney, Agent, or Firm*—Douglas K. Norman

[57] ABSTRACT

The present invention is a modified transcription control unit which contains the P2 enhancer of BK virus spaced closely to the upstream regulatory element of the major late promoter of adenovirus, the adenovirus-2 major late promoter, a poly-GT element positioned to stimulate said promoter and a DNA sequence containing the spliced tripartite leader sequence of adenovirus. The invention further comprises methods of using this modified transcription unit in cells expressing the adenovirus E1A gene product to produce useful substances. The invention further comprises methods to increase the levels of expression in stably transformed cells by performing a second transformation with a vector containing the modified transcription unit.

10 Claims, 18 Drawing Sheets

Restriction Site and Function Map of Plasmid pGT-h pGT-h

Restriction Site and Function Map of BK Virus

BK Virus

Restriction Site and Function Map of Plasmid pBKE1 pBKE1

Restriction Site and Function Map of Plasmid pBKneo1 pBKneo1

Restriction Site and Function Map of Plasmid pSV2cat pSV2cat

Restriction Site and Function Map of Plasmid pLPcat pLPcat

Restriction Site and Function Map of Plasmid pBLcat pBLcat

Restriction Site and Function Map of Plasmid pBKcat pBKcat

Restriction Site and Function Map of Plasmid pSBLcat pSBLcat

Restriction Site and Function Map of Plasmid pL133 pL133

Restriction Site and Function Map of Plasmid pLPC pLPC

Restriction Site and Function Map of Plasmid pLPC4 pLPC4

Restriction Site and Function Map of Plasmid pSV2hyg pSV2hyg

Restriction Site and Function Map of Plasmid pLPChyg1 pLPChyg1

Restriction Site and Function Map of Plasmid pBW32 pBW32

Restriction Site and Function Map of
Plasmid pLPChd1 pLPChd1

Restriction Site and Function Map of Plasmid pGTC pGTC

Restriction Site and Function Map of Plasmid pGT-d pGT-d

Restriction Site and Function Map of Plasmid pGT-h pGT-h

MODIFIED TRANSCRIPTION CONTROL UNIT AND USES THEREOF

This application is a division of application Ser. No. 08/160,450 filed Dec. 1, 1993 U.S. Pat. No. 5,573,938, which is a continuation of application Ser. No. 07/484,082, filed Feb. 23, 1990, now abandoned.

BACKGROUND OF THE INVENTION

The present invention utilizes the major late promoter (MLP) from human adenovirus type 2. The MLP contains a unique start site (cap site) for the initiation of transcription, which is directed by two regulatory elements, the TATA region at approximately −25 to −31 relative to the cap site and a binding site for the major late transcription factor at approximately −52 to −64.

The present invention further utilizes an enhancer sequence to increase expression from the major late promoter of adenovirus. Many enhancer sequences are known and their ability to enhance gene expression have been well described in the literature. The preferred enhancer in this invention is from the human polyomavirus BK, strain P2 (Berg et al., 1988, Nucl. Acids Res. 16:9057). Although this enhancer stimulates expression from the late promoter in many cell lines, it is most useful in cells expressing the immediate-early gene products of a large DNA virus, such as the Ela gene product of adenoviruses. Under these conditions, the Ela protein unexpectedly stimulates BKV enhancer activity (Grinnell et al., 1988, Mol. Cell. Biol. 8:3448).

Also important to the present invention is the copolymer poly(dG-dT).poly(dA-dC), "the GT element". This element is widely dispersed in the eukaryotic genome, and has been found in the non-translated regions and introns of a number of known genes. The element is capable of forming left-handed DNA and has been suggested to play a role in recombination and gene conversion events. While this element has been suggested to have weak enhancer activity with the SV40 early promoter, it does not have enhancer activity when used in conjunction with the MLP (Berg et al., 1989, Mol. Cell. Biol. 9:5248). Quite unexpectedly, an enhancer activity can be elicited from the GT element in the presence of an immediate-early gene product of a large DNA virus, such as the Ela protein of adenovirus.

Another element pertinent to the invention is a synthetically-derived DNA sequence representing the tripartite leader (TPL) sequence from human adenovirus type 2. This sequence is found on late viral mRNAs and is believed to facilitate the translation of such viral messages at late times in the virus + infectious cycle, but not during early times following infection (Zhang et al., 1989, J. Biol. Chem. 264:10679 and Dolph et al., 1988, J. Virol. 62:2059). However, it has also been reported that efficient transcription, not translation, is dependent on adenovirus TPL sequences at late times post-infection (Alonso-Caplen, 1988, J. Virol. 62:1606), and that the enhancement of transcription required the entire first leader (to nt41), in addition to 149 nucleotides of the adjacent intron. It has been reported that the TPL stabilized non-adenovirus mRNAs only within the environment of an adenovirus-infected cell during the late phase of the infectious cycle (Moore and Shenk, 1988, Nucl. Acids Res. 16:2247). Thus from the published literature, the TPL would not be expected to dramatically enhance gene expression except at late times following viral infection. The synthetic sequence of the present invention is not utilized in adenovirus-infected cells under late infection conditions. In contrast, the vectors are used in transformed cells expressing early viral functions. Further, the synthetic TPL does not contain the reported intron sequences required for transcriptional stimulation. Unexpectedly, the synthetic TPL of the present invention not only stimulates expression from the vectors of the present invention, but is approximately 2 fold more efficient than the previously disclosed nonspliced TPL sequence which does contain the sequence required for optimal transcription in late viral infected cells.

SUMMARY OF THE INVENTION

The present invention concerns a modified transcription control unit which comprises the P2 enhancer of BK virus spaced closely to the upstream regulatory element of the major late promoter of adenovirus (MLTF), the adenovirus 2 major late promoter, a poly-GT element positioned to stimulate said promoter and a DNA sequence containing the spliced tripartite leader sequence of adenovirus. This modified transcription unit, when positioned to drive the expression of a gene encoding a useful substance, is useful in greatly increasing the transcription and therefore expression levels of the useful substance. Another significant aspect of the present invention relates to a method of using the modified transcription control unit in the presence of an immediate-early gene product of a large DNA virus, such as the EIA gene product of adenovirus, for the purposes of increasing transcription and expression of recombinant genes in eukaryotic host cells. The versatility of the present expression vectors is demonstrated by the high-level expression driven by the modified transcription control unit of such diverse proteins as chloramphenicol acetyltransferase, human protein C and activated human protein C.

The practice of the invention results in increases in expression of human protein C in adenovirus-transformed cells. Such cells are especially preferred hosts for the production of fully gamma-carboxylated proteins, such as human protein C or activated human protein C. Consequently, a further aspect of the invention comprises an improved method for making gamma-carboxylated proteins.

Yet another important aspect of the present invention concerns a method for further increasing the expression of a useful gene product. This is performed by (a) obtaining a stable transformant of a cell clone which expresses and secretes a useful substance, but which does not contain a vector which comprises the modified transcription control unit of the present invention, then (b) transforming such a stably transformed clone with a vector which comprises a gene encoding the same useful substance, the expression of which is driven by the modified transcription control unit of the present invention. Dramatic increases in expression levels, as compared with clones which were not transformed with the second vector, were observed when the doubly-transformed cells were subcloned and cultured under conditions suitable for gene expression.

For purposes of the present invention, the following terms are as defined below:

Antibiotic—a substance produced by a micro-organism that, either naturally or with limited chemical modification, will inhibit the growth of or kill another microorganism or eukaryotic cell.

Antibiotic Resistance—Conferring Gene—a DNA segment that encodes an activity that confers resistance to an antibiotic.

ApR—the ampicillin-resistant phenotype or gene conferring same.

Cloning—the process of incorporating a segment of DNA into a recombinant DNA cloning vector.

CmR—the chloramphenicol-resistant phenotype or gene conferring same.

E1A—an immediate-early gene product of adenovirus which can activate a poly-GT element to express enhancer activity and can activate the BK virus enhancer.

ep—a DNA segment comprising the SV40 early promoter of the T-antigen gene, the T-antigen binding sites, and the SV40 origin of replication.

Eukaryotic promoter—any DNA sequence that functions as a promoter in eukaryotic cells.

GBMT transcription control unit—a modified transcription control unit which comprises the P2 enhancer element of BK virus spaced closely to the upstream regulatory element of the major late promoter of adenovirus (MLTF), the adenovirus-2 major late promoter and a poly-GT element positioned to stimulate said promoter and a DNA sequence encoding the spliced tripartite leader of adenovirus-2. The GMBT transcription control unit is best exemplified by the approximately 900 base pair HindIII cassette found in plasmid pGTC which is found in E. coli K-12 AG1/pGTC (NRRL B-18593).

GT—enhancer system—any poly-GT element linked to a promoter, such as MLP, in which the poly-GT element does not itself possess enhancer activity but is activated as an enhancer by an immediate-early gene product of a large DNA virus, such as the E1A gene product or by any similarly activating viral gene product.

HmR—the hygromycin-resistant phenotype or gene conferring same.

IVS—DNA encoding an intron, also called an intervening sequence.

Large DNA virus—a virus that infects eukaryotic cells and has a genome greater than ~10 kb in size, i.e., any of the pox viruses, adenoviruses, and herpes viruses.

MLP—the major late promoter of adenovirus, which is also referred to herein as the adenovirus late promoter, adenovirus-type-2 late promoter, or Ad2 late promoter.

MLTF binding site—the site in adenovirus DNA where the major late transcription factor (MLTF) binds; the MLTF is required for MLP activity.

NeoR—the neomycin resistance-conferring gene, which can also be used to confer G418 resistance in eukaryotic host cells.

ori—a plasmid origin of replication.

pA—a DNA sequence encoding a polyadenylation signal.

Poly-GT element—a DNA sequence of $(GT)_n$-$(CA)_n$, which is illustrated herein by a sequence where n is 21, but which can also refer to sequences of varying lengths where n is greater or less than 21, and may refer to chemically synthesized $(GT)_n$-$(CA)_n$ sequences or human genomic DNA fragments containing a $(GT)_n$-$(CA)_n$ tract.

Promoter—a DNA sequence that directs transcription of DNA into RNA.

Recombinant DNA Cloning Vector—any autonomously replicating or integrating agent that comprises a DNA molecule to which one or more additional DNA segments can be or have been added.

Recombinant DNA Expression Vector—any recombinant DNA cloning vector comprising a promoter and associated insertion site, into which a DNA sequence that encodes a useful product can be inserted and expressed.

Recombinant DNA Vector—any recombinant DNA cloning or expression vector.

Replicon—any DNA sequence that controls the replication of a recombinant DNA vector.

Restriction Fragment—any linear DNA generated by the action of one or more restriction enzymes.

rRNA—ribosomal ribonucleic acid.

Sensitive Host Cell—a host cell that cannot grow in the presence of a given antibiotic or other toxic compound without a DNA segment that confers resistance thereto.

Structural Gene—any DNA sequence that encodes a polypeptide, inclusive of that DNA encoding the start and stop codons.

TcR—the tetracycline-resistance phenotype or gene conferring same.

Transformant—a recipient host cell that has undergone transformation.

Transformation—the introduction of DNA into a recipient host cell.

tRNA—transfer ribonucleic acid.

DETAILED DESCRIPTION OF THE INVENTION

The present invention concerns a novel modified transcription control unit, designated as the GBMT unit, which comprises the P2 enhancer of BK virus spaced closely to the upstream regulatory element of the major late promoter of adenovirus (MLTF), the adenovirus-2 major late promoter, a poly-GT element positioned to stimulate said promoter and a DNA sequence encoding the spliced tripartite leader sequence of adenovirus. The GMBT unit will drive high levels of expression of a useful substance in eukaryotic cells when the gene encoding said useful substance is properly positioned for expression.

The present invention also relates to methods for expressing useful substances in eukaryotic host cells by transforming said host cells with a recombinant DNA vector that encodes a useful substance in such a position that transcription can be controlled by the GBMT control unit. An unexpectedly high level of expression can be obtained when the transformed host cell expresses an immediate early gene product of a large DNA virus. Examples of such immediate-early gene products include the adenovirus E1A protein, the adenovirus E1B protein, the pseudorabies virus IE protein and the herpes simplex virus ICP4 protein. The gene encoding such an immediate-early gene product may be co-transformed into the host cell on a separate vector from the GBMT unit or may be transformed into the host cell on the same vector as the GBMT unit. Alternatively, and most preferably, the host cell may be an established cell that already expresses the immediate-early gene product. Those skilled in the art recognize that many established cell lines express an immediate-early gene product and that such cell lines are especially useful in the present method.

Yet another important aspect of the present invention relates to methods to greatly increase the levels of expression of a useful substance in a stably transformed cell line. A host cell is first stably transformed with an expression vector which does not comprise the GBMT unit, then subclones which demonstrate the highest levels of expression are selected. These subclones are then transformed a second time with a vector which comprises a gene encoding the useful substance, the expression of which is driven by the GBMT unit. Clones and subclones which secrete unexpectedly high levels of the useful substance may then be selected.

The expression vectors of the present invention were constructed so that DNA molecules encoding useful substances can be or have been readily inserted into the vectors in the correct position for expression. Furthermore, the GBMT transcription unit has been constructed to form a "cassette," which can be isolated from the expression vectors on a relatively small restriction fragment. The cassette can be readily shuttled between a variety of expression vectors. The expression vectors specifically exemplified herein utilize the GBMT unit that drives transcription in the method of the present invention.

Figure 16:
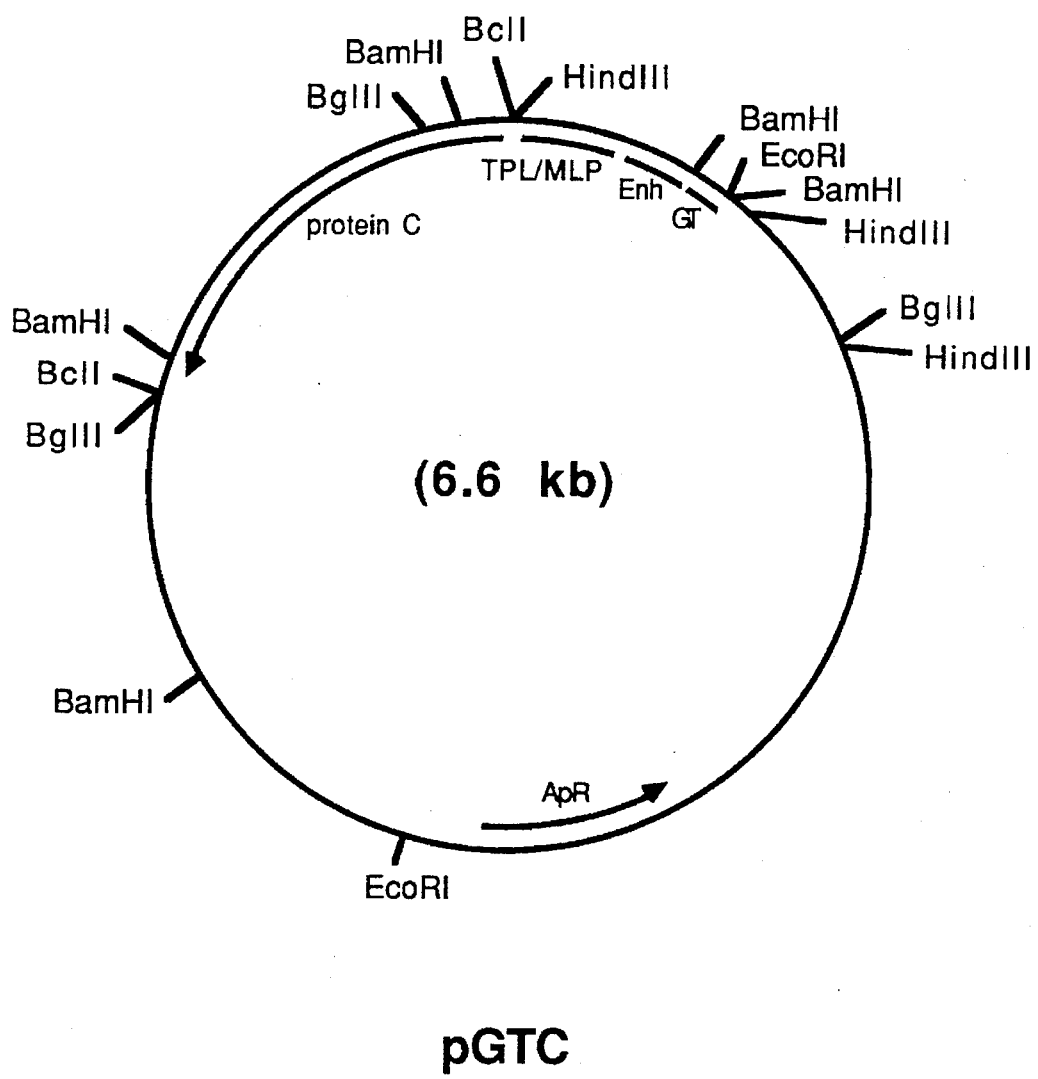
FIG. 16 is a restriction site and function map of plasmid pGTC.

One such expression vector of the present invention is plasmid pGTC which comprises the GBMT unit positioned to drive the transcription and expression of the gene encoding human protein C. The gene encoding human protein C is disclosed and claimed in Bang et al., U.S. Pat. No. 4,775,621, issued Oct. 4, 1988, the entire teaching of which is herein incorporated by reference. Plasmid pGTC can be conventionally isolated from *Escherichia coli* K12 AG1/pGTC, a culture deposited on Jan. 18, 1990 and made part of the permanent stock culture collection of the Northern Regional Research Laboratories in Peoria, Ill., *E. coli* K12 AG1/pGTC can be obtained under the accession number NRRL B-18593. A restriction site and function map of plasmid pGTC is presented in FIG. 16 of the accompanying drawings.

Figure 17:
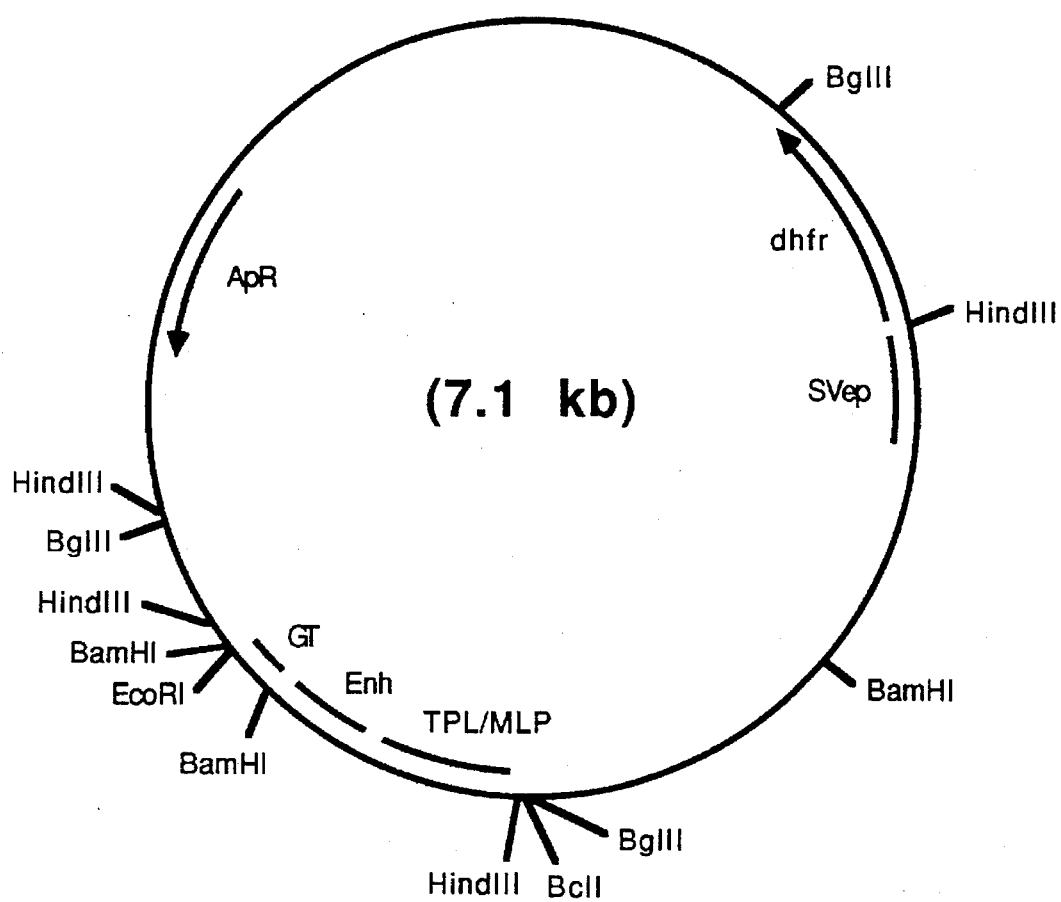
FIG. 17 is a restriction site and function map of plasmid pGT-d.

Other plasmids of the present invention also comprise the GBMT unit. Plasmid pGT-d comprises the GBMT unit positioned such that the insertion of a gene encoding a useful substance may be accomplished using a unique BclI site downstream from the GBMT cassette, following DNA preparation in a dam⁻ strain of *E. coli*. Plasmid pGT-d also contains the murine dhfr gene which is useful as a selectable marker because it confers resistance to methotrexate. Plasmid pGT-d can be isolated from *E. coli* K12 AG1/pGT-d, which was deposited on Jan. 18, 1990 at the NRRL and is available under the accession number NRRL B-18591. A restriction site and function map of plasmid pGT-d is presented in FIG. 17 of the accompanying drawings.

Figure 18:
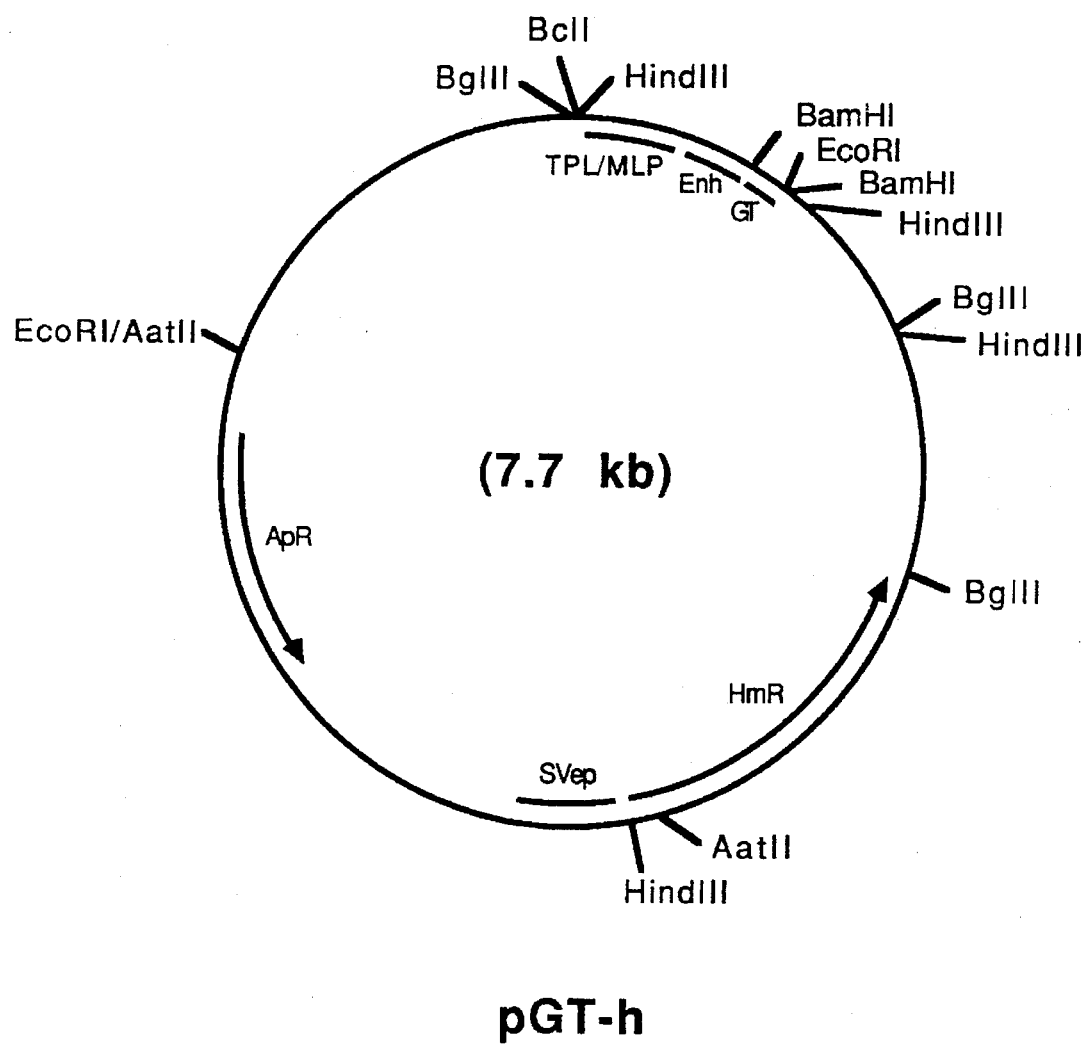
FIG. 18 is a restriction site and function map of plasmid pGT-h.

Plasmid pGT-h also contains the GBMT unit positioned such that the insertion of a gene encoding a useful product may be accomplished using the unique BclI site downstream from the GBMT cassette following preparation of DNA from a dam⁻ strain of *E. coli*. Plasmid pGT-h, however, contains a gene encoding the hygromycin resistance determinant. Plasmid pGT-h can be isolated from *E. coli* K12 AG1/pGT-h, which also was deposited with the NRRL on Jan. 18, 1990. The culture is available under accession number NRRL B-18592. A restriction site and function map of plasmid pGT-h is presented in FIG. 18 of the accompanying drawings.

The GBMT unit found in the approximately 900 base pair HindIII cassette of plasmids pGTC, pGT-d and pGT-h comprises the sequence:

```
AAGCTTTTCT CATTAAGGGA AGATTTCCCC

AGGCAGCTCT TTCAAGGGAT

CCTCGAGAAT TCACACACAC ACACACACAC

ACACACACAC ACACACACAC

ACACTAGAGG ATCCCTAAAA GGTCCATGAG

CTCCATGGAT TCTTCCCTGT

TAAGAACTTT ATCCATTTTT GCAAAAATTG

CAAAAGAATA GGGATTTCCC

CAAATAGTTT TGCTAGGCCT CAGAAAAAGC

CTCCACACCC TTACTACTTG

AGAGAAAGGG TGGAGGCAGA GGCGGCCTCG

GCCTCTTATA TATTATAAAA

AAAAAGGCCA CAGGGAGGAG CTGCTTACCC

ATGGAATGCA GCCAAACCAT

GACCTCAGGA AGGAAAGTGC ATGACTGGGC

AGCCAGCCAG TGGCAGTTAA

TAAGCAGCCA GACAGACATT TGCTTACCCA

TGGAATGCAG CCAAACCATG

ACCTCAGGAA GGAAAGTGCA TGACTGGGCA

GCCAGCCAGT GGCAGTTAAT

AAGCAGCAGC CAGACAGACA TGTTTTGCGA

GCCTAGTCGC CCTCTTCGGC
```

-continued

```
ATCAAGGAAG GTGATTGGTT TATAGGTGTA
                      GGCCACGTGA CCGGGTGTTC
CTGAAGGGGG GCTATAAAAG GGGGTGGGGG
                      CGCGTTCGTC CTCACTCTCT
TCCGCATCGC TGTCTGCGAG GGCCAGCTGT
                      TGGGCTCGCG GTTGAGGACA
AACTCTTCGC GGTCTTTCCA GTACTCTTGG
                      ATCGGAAACC CGTCGGCCTC
CGAACGTACT CCGCCACCGA GGGACCTGAG
                      CGAGTCCGCA TCGACCGGAT
CGGAAAACCT CTCGAGAAAG GCGTCTAACC
                      AGTCACAGTC GCAAGCTT.
```

This cassette contains the optimal spacing of the BK enhancer with the adenovirus 2 major late promoter, and contains the poly GT element upstream of the BK enhancer. The BK enhancer could be as far away as 200 base pairs from the major late promoter, and the poly GT element may be located elsewhere on the plasmid. Additionally, the cassette utilizes the synthetic tripartite leader sequence which is about two times more efficient than the nonspliced version previously disclosed by Grinnell in European Patent Application 87303083.7, the entire teaching of which is herein incorporated by reference.

Specifically, nucleotides 62 through 104 of the GBMT HindIII cassette comprise a poly GT (AC) element which is useful to increase gene expression in the presence of trans-acting gene products such as an immediate-early gene product of a large DNA virus. The use of such GT elements in eukaryotic expression is disclosed in Grinnell et al., U.S. patent application Ser. No. 07/255,203, filed Sep. 3, 1988, abandoned, the entire teaching of which is herein incorporated by reference.

Nucleotides 306 through 507 of the GBMT HindIII cassette comprise the BK virus P2 enhancer element which is a cis-acting element that increases transcription from the adenovirus major late promoter in accordance with the teaching of Grinnell, U.S. patent application Ser. No. 07/129,028, filed Dec. 4, 1987, abandoned, the entire teaching of which is herein incorporated by reference. The BK enhancer is a defined segment of DNA that consists of three repeated sequences (in the prototype), although a wide variety of BK enhancer variants are known. The BK enhancer found in the GBMT cassette of the present invention contains the 68 base pair repeat running from base 306 to base 376 and again from base 409 to base 475. The 32 base pair repeat runs from base 377 to base 408, then again from base 476 to base 507.

The MLTF binding site of the GBMT cassette is found beginning at base 581 and comprises the sequence: 5'-GGCCACGTGACC-3'. The close positioning of the MLTF binding site of the adenovirus major late promoter near the P2 enhancer of BK virus helps to increase the transcription level arising from the use of the GMBT unit. The "TATA" region of the MLP is found between bases 612 and 620 of the cassette, while the synthetic tripartite leader sequence of adenovirus is located between bases 643 and 844.

Various vectors comprising several different promoter systems were transformed into host cells to exemplify the strength of the GBMT transcription unit of the present invention. Plasmids pLPC-hd, pLPC-hyg, pLPC-dhfr and pBL2-CAT all contain the BL promoter system disclosed by Grinnell in U.S. patent application Ser. No. 07/368,700, filed Jun. 20, 1989, abandoned. The construction protocols for each of these plasmids are disclosed in detail in the accompanying Examples. The BL promoter system utilizes the BK virus enhancer in conjunction with the adenovirus 2 major late promoter.

Plasmids pLAPC-IRS and pSBL-CAT contain the SBL promoter system disclosed by Grinnell in 07/368,700 supra. The construction of plasmid pLAPC-IRS, which contains the gene encoding activated human protein C, is disclosed in Bang et al., U.S. patent application Ser. No. 07/129,027, filed Dec. 4, 1987, U.S. Pat. No. 4,992,373 the teaching of which is herein incorporated by reference. The SBL promoter system contains the tandem SV40 enhancer-BK enhancer in conjunction with the adenovirus major late promoter.

Plasmid pLP-CAT contains the adenovirus late promoter and no enhancer sequence. Plasmid pGTC contains the GBMT unit positioned to drive expression of the gene encoding human protein C, while plasmid pGTAC-h contains the GBMT transcription unit positioned to drive expression of the gene encoding activated human protein C. Each of the plasmids described supra was transformed into human 293 cells, which is a stably transformed cell line which expresses the adenovirus E1A gene product. Skilled artisans will recognize that other cell lines which also express the E1A gene product, such as Syrian Hamster AV12-664 cells, are also available and useful in the methods of the present invention.

Upon transformation into 293 cells, the various vectors were either checked for the immediate expression of gene product (3 day transient expression) or cultured with selective drug to obtain stable transformants. The methods for analyzing gene products from such vectors are well known in the art and are disclosed in Grinnell et al., 1987, *Biotechnology* 5:1189–1192, and Grinnell et al., 1986, *Mol. Cell. Biol.* 6:3596–3605, the teachings of which are herein incorporated by reference. Table I shows the results of transient expression assays while Table II demonstrates the analysis of zymogen and activated human protein C expression from stably integrated plasmids.

TABLE I

Analysis of Promoter Strength
(Transient Assay)

| Promoter | Vector | Relative Level of Expression |
| --- | --- | --- |
| MLP | pLP-CAT | 1 |
| BL | pBL2-CAT(pLPC-hd) | 73[a] |
| GBMT | pGTC | 5275 |
| SBL | pSBL-CAT | 23[a] |

[a]Relative level of promoter strength between MLP, SBL and BL was determined by chloramphenicol acetyltransferase (CAT) enzyme with CAT as an indicator gene. Relative promoter strength between BL and GBMT was determined with human protein C as an indicator gene in a standard ELISA assay.

TABLE II

Analysis of Human Protein C Expression from Stably Integrated Plasmids

| Promoter | Vector | x̄(ng/ml)[a] | range (ng/ml) | x̄ng/10⁶ cells |
|---|---|---|---|---|
| | | Activated Protein C | | |
| SBL | pLAPC-IRS | 33(n = 12) | 13–69 | 26 |
| GBMT | pGTAC-h | 1460(n = 22) | 652–3117 | 622 |
| | | Human Protein C | | |
| BL | pLPC-hd pLPC-hyg pLPC-dhfr | 120(n = 30) | 12—480 | 95 |
| GBMT | pGTC | 2930(n − 48) | 270–5095 | 2340 |

[a]cultures in 0.9 cm² surface area grown to confluence

Another aspect of the present invention is demonstrated in Examples 11 and 12, wherein stably transformed cell lines producing human protein C were enhanced by transformation with the pGTC vector. Plasmid pLPC was first stably transformed into 293 cells and subclones which secreted 2 to 3 times more human protein C than the general background population were selected. These stably transfected cells were then re-transformed with plasmid pGTC, which contains a gene encoding human protein C driven by the GBMT transcription unit. Quite unexpectedly, many more high producing clones were discovered than with a single transformation of 293 cells with pGTC. Furthermore the doubly transformed cells secreted between 3.5 to 6.3 times more human protein C as the parent cell line transformed only with vector pLPC following selection for the highest producing clone.

The following Examples more fully describe the vectors, methods, compounds and recombinant organisms of the present invention. Those skilled in the art will recognize that the particular reagents, equipment and procedures described in the Examples are merely illustrative and do not limit the present invention.

EXAMPLE 1

Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about $10^5$ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, Va. 22101, under catalogue number 0-100 or from M.A. Bioproducts under catalogue number 70-151. Alternatively, BK virus can be propagated in Vero cells (ATCC catalogue number CCL81).

About five 75 mm² polystyrene flasks comprising confluent monolayers of about $10^6$ PHEK cells are used to prepare the virus. About 1 ml of BK virus at a titer of $10^5$ pfu/ml is added to each flask, which is then incubated at 37° C. for one hour, and then, fresh culture medium (Dulbecco's Modified Eagle's Medium, Gibco, supplemented with 10% fetal bovine serum) is added, and the infected cells are incubated at 37° C. for 10–14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000 Xg. The virus in 1 liter of supernatant fluid is precipitated and collected by the addition of 100 g of PEG-6000, incubation of the solution for 24 hours at 4° C., and centrifugation at 5000 Xg for 20 minutes. The pellet is dissolved in 0.1X SSC buffer (1XSSC=0.15M NaCl and 0.015M NaCitrate, pH=7) at 1/100th of the original volume. The virus suspension is layered onto a 15 ml solution of saturated KBr in a tube, which is centrifuged at 75,000 Xg for 3 hours. Two bands are evident in the KBr solution after centrifugation. The lower band, which contains the complete virion, is collected and desalted on a Sephadex® G-50 column (Sigma Chemical Co., P.O. Box 14508, St. Louis, Mo. 63178) using TE (10 mM Tris-HCl, pH=7.8, and 1 mM EDTA) as an elution buffer.

Sodium dodecyl sulfate (SDS) is added to the solution of purified virions obtained from the column to a concentration of 1%; pronase is added to a concentration of 100 µg/ml, and the solution is incubated at 37° C. for 2 hours. Cesium chloride is then added to the solution to a density of 1.56 g/ml, and ethidium bromide is added to the solution to a final concentration of 100 µg/ml. The solution is centrifuged in a Sorvall (DuPont Inst. Products, Biomedical Division, Newton, Conn. 06470) 865 rotor or similar vertical rotor at 260,000 Xg for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15M, adding two volumes of ethanol, incubating the solution at −70° C. for at least 2 hours, and centrifuging the solution at 12,000 Xg for 10 minutes. The resulting pellet of BK virus DNA is suspended in TE buffer at a concentration of 1 mg/ml.

EXAMPLE 2

Construction of Plasmids pBKE1 and pBKE2

About one µg of the BK virus DNA prepared in Example 1 in one µl of TE buffer was dissolved in 2 µl of 10X EcoRI buffer (1.0M Tris-HCl, pH=7.5; 0.5M NaCl; 50 mM MgCl₂; and 1 mg/ml BSA) and 15 µl of H₂O. About 2 µl (~10 units; all enzyme units referred to herein, unless otherwise indicated, refer to the unit definitions of New England Biolabs, 32 Tozer Road, Beverly, Mass. 01915-9990, although the actual source of the enzymes may have been different) of restriction enzyme EcoRI were added to the solution of DNA, and the resulting reaction was incubated at 37° C. for two hours About 1 µg of plasmid pUC8 (available from Pharmacia P-L Biochemicals, 800 Centennial Ave., Piscataway, N.J. 08854) in 1 µl of TE buffer was digested with EcoRI in substantial accordance with the procedure used to prepare the EcoRI-digested BK virus DNA. The EcoRI-digested plasmid pUC8 DNA was diluted to 100 µl in TE buffer; ~0.06 units of calf-intestinal alkaline phosphatase were added to the solution, and the resulting reaction was incubated at 37° C. for 30 minutes. The solution was adjusted to contain 1X SET (5 mM Tris-HCl, pH=7.8; 5 mM EDTA; and 150 mM NaCl), 0.3M NaOAc, and 0.5% SDS and then incubated at 65° C. for 45 minutes. The phosphatase treatment prevents the pUC8 DNA from self ligating.

The EcoRI-digested BK virus and plasmid pUC8 DNA were extracted first with buffered phenol and then with chloroform. The DNA was collected by adjusting the NaCl concentration of each DNA solution to 0.25M, adding two volumes of ethanol, incubating the resulting mixtures in a dry ice-ethanol bath for 5 minutes, and centrifuging to pellet the DNA. The supernatants were discarded, and the DNA pellets were rinsed with 70% ethanol, dried, and resuspended in 10 µl and 30 µl of TE buffer for the BK and plasmid pUC8 samples, respectively.

Figure 1:
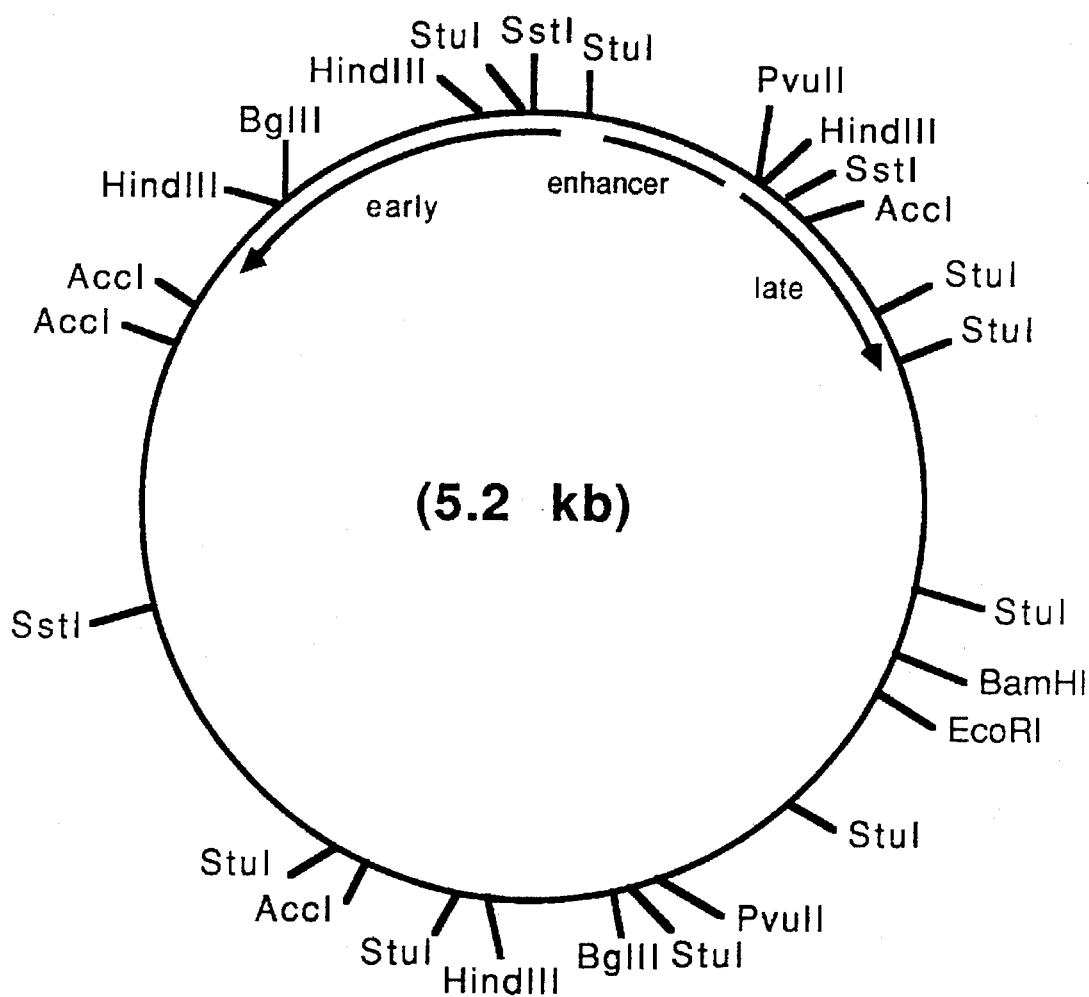
FIG. 1 is a restriction site and function map of BK virus. For purposes of this disclosure, the Figures are not drawn exactly to scale.
Figure 2:
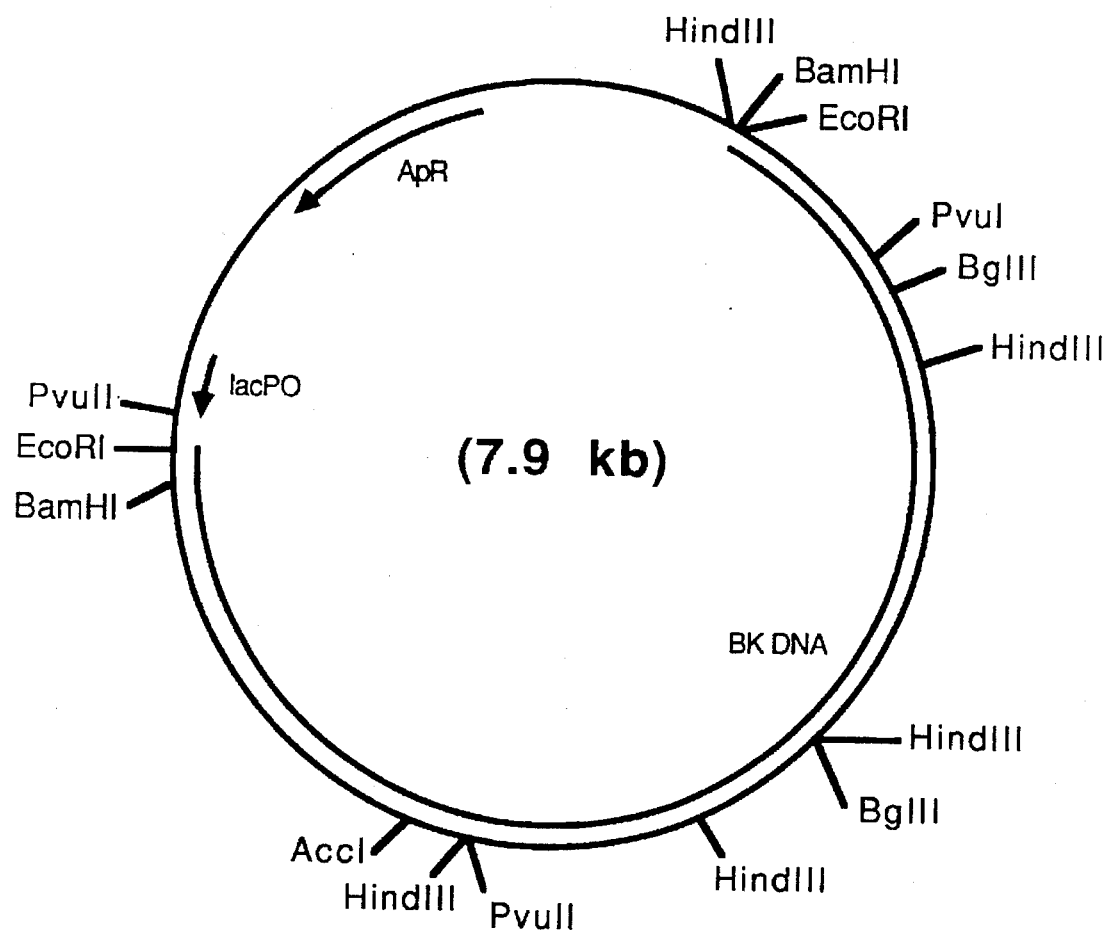
FIG. 2 is a restriction site and function map of plasmid pBKE1.

About 3 µl of H$_2$O and 1 µl of 10X ligase buffer (0.5M Tris-HCl, pH=7.8; 100 mM MgCl$_2$; 200 mM DTT; 10 mM ATP; and 0.5 mg/ml BSA) were added to a mixture of 2 µl of the EcoRI-digested BK virus and 1 µl of the EcoRI-digested plasmid pUC8 DNA. One µl (~1000 units) of T4 DNA ligase were added to the solution of DNA, and the resulting reaction was incubated at 16° C. overnight. The ligated DNA constituted the desired plasmids pBKE1 and pBKE2, which differ only with respect to the orientation of the inserted BK virus DNA. A restriction site and function map of plasmid pBKE1 is presented in FIG. 2 of the accompanying drawings.

A 50 ml culture of *E. coli* K12 JM103, available from Pharmacia P-L Biochemicals, in L-broth was grown to an optical density at 650 nanometers (O.D.$_{650}$) of approximately 0.4 absorbance units. The culture was chilled on ice for ten minutes, and the cells were collected by centrifugation. The cell pellet was resuspended in 25 ml of cold 100 mM MgCl$_2$ and incubated on ice for 25 minutes. The cells were once again pelleted by centrifugation, and the pellet was resuspended in 2.5 ml of cold 100 mM CaCl$_2$ and incubated for 30 minutes on ice. After the incubation, the cells are competent for the uptake of transforming DNA.

Two hundred µl of this cell suspension were mixed with the ligated DNA prepared above and incubated on ice for 30 minutes. At the end of this period, the cells were placed in a water bath at 42° C. for 2 minutes and then returned to the ice for an additional 10 minutes. The cells were collected by centrifugation and resuspended in one ml of L broth and incubated at 37° C. for 1 hour.

Aliquots of the cell mixture were plated on L-agar (L-broth with 15 grams of agar per liter) plates containing 100 µg ampicillin/ml, 40 µg X-gal/ml, and 40 µg IPTG/ml. The plates were incubated at 37° C. overnight. Colonies that contain a plasmid without an insert, such as *E. coli* K12 JM103/pUC8, appear blue on these plates. Colonies that contain a plasmid with an insert, such as *E. coli* K12 JM103/pBKE1, are white. Several white colonies were selected and screened by restriction enzyme analysis of their plasmid DNA for the presence of the ~5.2 kb EcoRI restriction fragment of BK virus. Plasmid DNA was obtained from the *E. coli* K12 JM103/pBKE1 and *E. coli* K12 JM103/pBKE2 cells in substantial accordance with the procedure for isolating plasmid DNA that is described in the following Example, although the procedure is done on a smaller scale, and the CsCl gradient steps are omitted, when the plasmid DNA is isolated only for restriction enzyme analysis.

EXAMPLE 3

Construction of Plasmids pBKneo1 and pBKneo2

*E. coli* K12 HB101/pdBPV-MMTneo cells are obtained in lyophil form from the American Type Culture Collection under the accession number ATCC 37224. The lyophilized cells are plated on L-agar plates containing 100 µg/ml ampicillin and incubated at 37° C. to obtain single colony isolates.

One liter of L broth (10 g tryptone, 10 g NaCl, and 5 g yeast extract per liter) containing 50 µg/ml ampicillin was inoculated with a colony of *E. coli* K12 HB101/pdBPV-MMTneo and incubated in an air-shaker at 37° C. until the O.D.$_{590}$ was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

The culture was centrifuged in a Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was discarded, and the cell pellet was frozen in a dry ice-ethanol bath and then thawed. The thawed cell pellet was resuspended in 10 ml of a solution of 25% sucrose and 50 mM EDTA. About 1 ml of a 5 mg/ml lysozyme solution; 3 ml of 0.25M EDTA, pH=8.0; and 100 µl of 10 mg/ml RNAse A were added to the solution, which was then incubated on ice for 15 minutes. Three ml of lysing solution (prepared by mixing 3 ml 10% Triton-X 100; 75 ml 0.25M EDTA, pH=8.0; 15 ml of 1M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, Ill. 60646) and by extraction with buffered phenol. About 30.44 g of CsCl and ~1 ml of a 5 mg/ml ethidium bromide solution were added to the cell extract, and then, the volume of the solution was adjusted to 40 ml with TES buffer. The solution was decanted into a VTi50 ultra-centrifuge tube (Beckman), which was then sealed and centrifuged in a VTi50 rotor at 42,000 rpm for ~16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. Two volumes of ethanol were then added to the solution, which was then incubated overnight at −20° C. The plasmid DNA was pelleted by centrifuging the solution in an SS34 rotor (Sorvall) for 15 minutes at 10,000 rpm.

The ~1 mg of plasmid pdBPV-MMTneo DNA obtained by this procedure was suspended in 1 ml of TE buffer and stored at −20° C. The foregoing plasmid isolation procedure is generally used when large amounts of very pure plasmid DNA are desired. The procedure can be modified to rapidly obtain a smaller, less pure amount of DNA, such as is needed when screening transformants for the presence of a given plasmid, by using only about 5 ml of cultured cells, lysing the cells in an appropriately scaled-down amount of lysis buffer, and replacing the centrifugation steps with phenol and chloroform extractions.

About 5 µg (5 µl) of the plasmid pdBPV-MMTneo DNA prepared above and five µg (5 µl) of the BK virus DNA prepared in Example 1 were each digested at 37° C. for 2 hours in a solution containing 2 µl of 10X BamHI buffer (1.5M NaCl; 60 mM Tris-HCl, pH=7.9; 60 mM MgCl$_2$; and 1 mg/ml BSA), 1 µl of restriction enzyme BamHI, and 7 µl of H$_2$O. The reaction was stopped by an extraction with an equal volume of phenol, followed by two extractions with chloroform. Each BamHI-digested DNA was then precipitated, collected by centrifugation, and resuspended in 5 µl of H$_2$O.

Figure 3:
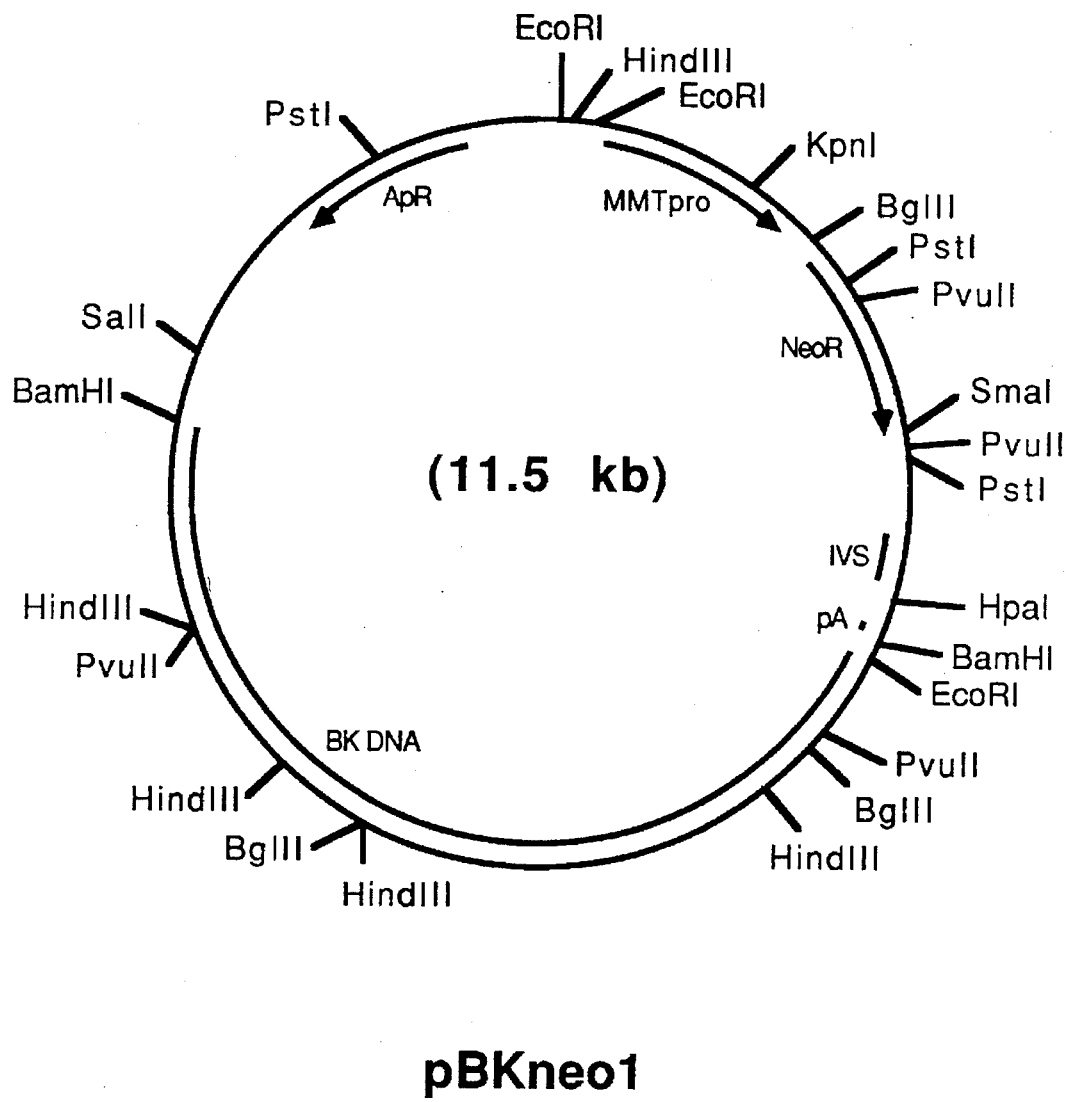
FIG. 3 is a restriction site and function map of plasmid pBKneo1.

About 1 μl of 10X ligase buffer was added to a mixture of BamHI-digested plasmid pdBPV-MMTneo (1 μl) and BamHI-digested BK virus DNA (1 μl). After 1 μl (~1000 units) of T4 DNA ligase and 6 μl of H$_2$O were added to the mixture of DNA, the resulting reaction was incubated at 16° C. overnight. The ligated DNA constituted the desired plasmids pBKneo1 and pBKneo2, which differ only with respect to the orientation of the BK virus DNA. A restriction site and function map of plasmid pBKneo1 is presented in FIG. 3 of the accompanying drawings.

E. coli K12 HB101 cells are available in lyophilized form from the Northern Regional Research Laboratory under the accession number NRRL B-15626. E. coli K12 HB101 cells were cultured, made competent for transformation, and transformed with the ligated DNA prepared above in substantial accordance with the procedure of Example 2. The transformed cells were plated on L-agar plates containing 100 μg/ml ampicillin. E. coli K12 HB101/pBKneo1 and E. coli K12/pBKneo2 transformants were identified by their ampicillin-resistant phenotype and by restriction enzyme analysis of their plasmid DNA.

EXAMPLE 4

Construction of Plasmid pBLcat

A. Construction of Intermediate Plasmid pLPcat

The virion DNA of adenovirus 2 (Ad2) is a double-stranded linear molecule about 35.94 kb in size. The Ad2 late promoter can be isolated on an ~0.316 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL) are dissolved in 80 μl of H$_2$O and 10 μl of 10X BalI buffer (100 mM Tris-HCl, pH=7.6; 120 mM MgCl$_2$; 100 mM DTT; and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long-wave ultraviolet (UV) light. One method to isolate DNA from agarose is as follows. A small slit is made in the gel in front of the desired fragment, and a small piece of NA-45 DEAE membrane (Schleicher and Schuell, Keene, N.H. 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl; 0.1 mM EDTA; and 20 mM Tris-HCl, pH=8). Next, the membrane is placed in a small tube and immersed in high-salt buffer (1M NaCl; 0.1 mM EDTA; and 20 mM Tris-HCl, pH=8) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25M, and then three volumes of cold, absolute ethanol are added to the solution. The resulting solution is mixed and placed at −70° C. for 10–20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 μg of the desired restriction fragment of Ad2. The purified fragment obtained is dissolved in 10 μl of TE buffer.

About 6 μl of H$_2$O and 2 μl of 10X AccI buffer (60 mM NaCl; 60 mM Tris-HCl, pH=7.5; 60 mM MgCl$_2$; 60 mM DTT; and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of H$_2$O and 2 μl of 10X PvuII buffer (600 mM NaCl; 60 mM Tris-HCl, pH=7.5; 60 mM MgCl$_2$; 60 mM DTT; and 1 mg/ml BSA). After the addition of about 2 μl (about 10 units) of restriction enzyme PvuII to the solution of DNA, the reaction is incubated at 37° C. for 2 hours.

The AccI-PvuII -digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM NH$_4$OAc; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of H$_2$O.

About 0.25 μg (in 0.5 μl) of BclI linkers (5'-CTGATCAG-3', available from New England Biolabs), which had been kinased in substantial accordance with the procedure described in Example 10A, below, was added to the solution of the ~0.32 kb AccI-PvuII restriction fragment, and then, 1 μl (~1000 units) of T4 DNA ligase and 1 μl of 10X ligase buffer were added to the solution of DNA, and the resulting reaction was incubated at 16° C. overnight. The BclI linkers could only ligate to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

Figure 4:
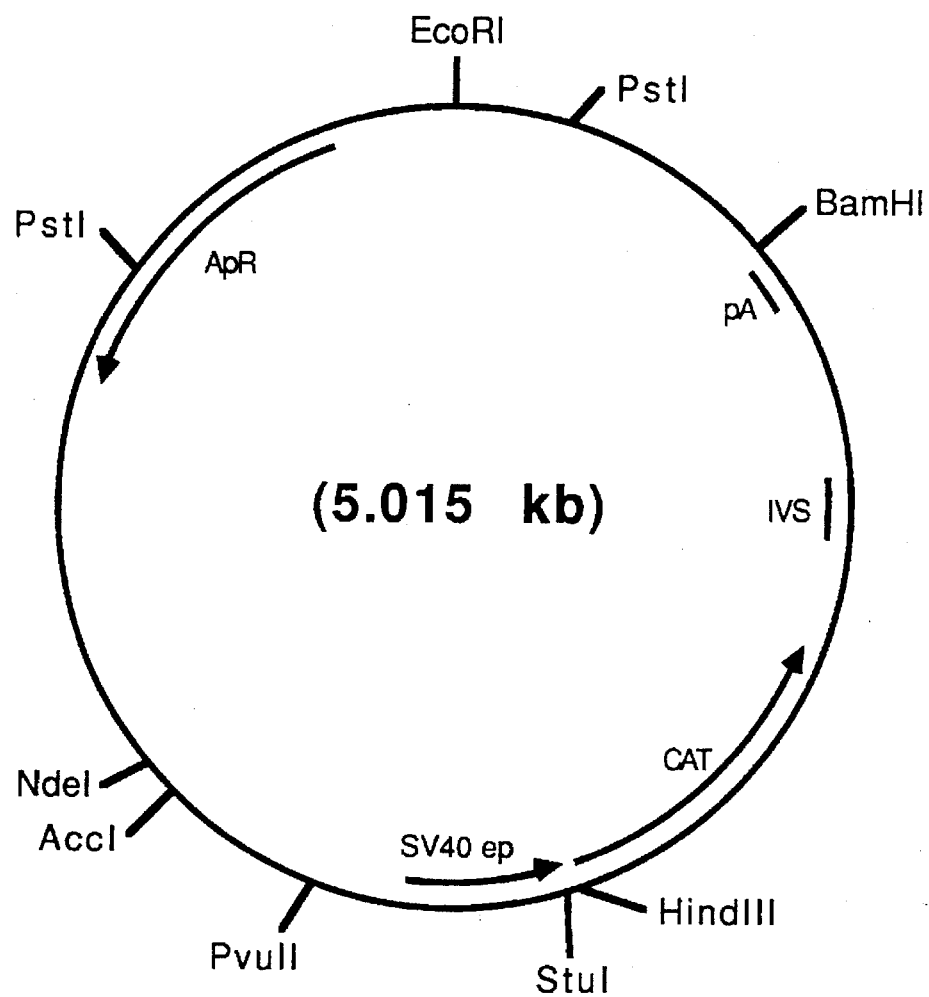
FIG. 4 is a restriction site and function map of plasmid pSV2cat.

E. coli K12 HB101/pSV2cat cells are obtained in lyophilized form from the ATCC under the accession number ATCC 37155, and plasmid pSV2cat DNA was isolated from the cells in substantial accordance with the procedure of Example 3. A restriction site and function map of plasmid pSV2cat is presented in FIG. 4 of the accompanying drawings. About 1 mg of plasmid pSV2cat DNA is obtained and dissolved in 1 ml of TE buffer. About 3 μg (3 μl) of the plasmid pSV2cat DNA were added to 2 μl of 10X AccI buffer and 16 μl of H$_2$O, and then, 3 μl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 µl of 10X StuI buffer (1.0M NaCl; 100 mM Tris-HCl, pH=8.0; 100 mM MgCl₂; 60 mM DTT; and 1 mg/ml BSA), 5 µl of H₂O, and about 2 µl (about 10 units) of restriction enzyme StuI. The resulting reaction was incubated at 37° C. for 2 hours. The reaction was terminated by extracting the reaction mixture once with phenol, then twice with chloroform. About 0.5 µg of the desired fragment was obtained and dissolved in 20 µl of TE buffer.

Figure 5:
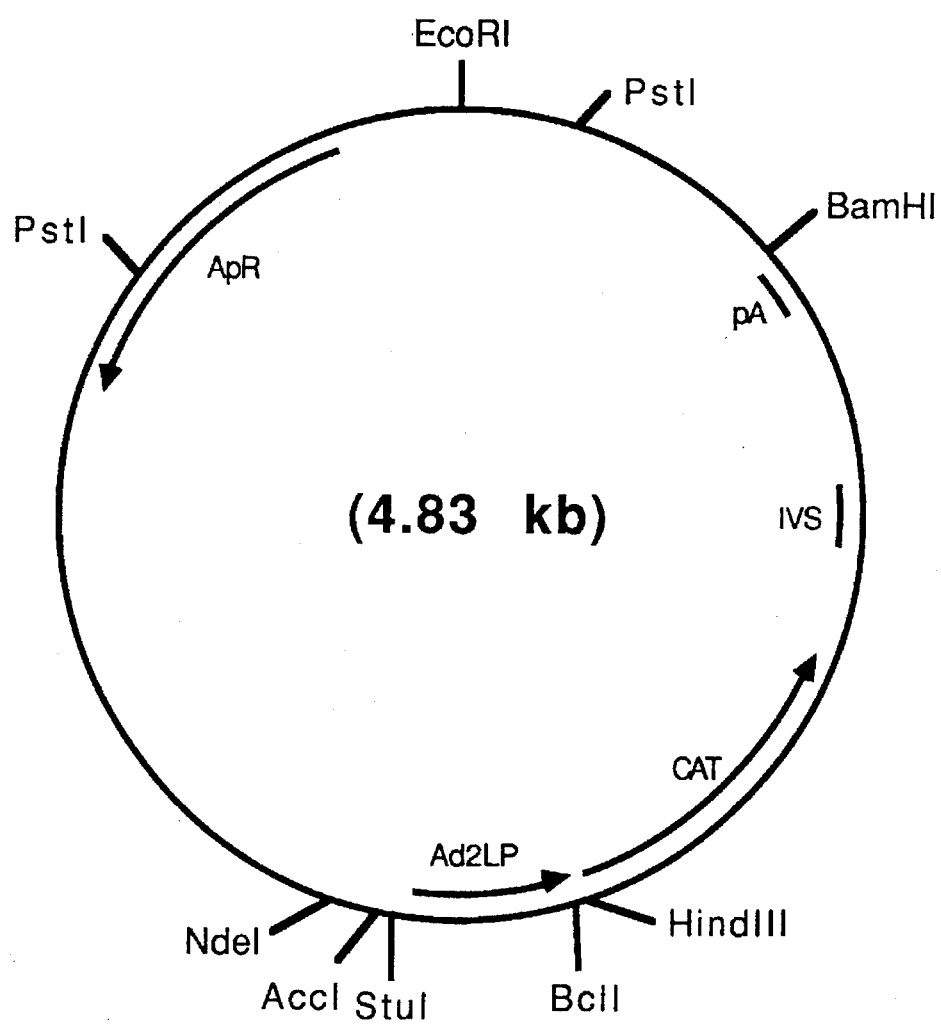
FIG. 5 is a restriction site and function map of plasmid pLPcat.

About 4 µl of the AccI-StuI-digested plasmid pSV2cat DNA were mixed with about 7 µl of the ~0.32 kb AccI-PvuII (with BclI linkers attached) restriction fragment of Ad2, and after the addition of 3 µl of 10X ligase buffer, 15 µl of H₂O, and 2 µl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene. A restriction site and function map of plasmid pLPcat is presented in FIG. 5 of the accompanying drawings.

The ligated DNA was used to transform *E. coli* K12 HB101 cells in substantial accordance with the procedure of Example 2. The transformed cells were plated on L agar containing 50 µg/ml ampicillin; restriction enzyme analysis of plasmid DNA was used to identify the *E. coli* K12 HB101/pLPcat transformants. Plasmid pLPcat DNA was isolated from the transformants for use in subsequent constructions in substantial accordance with the plasmid isolation procedure described in Example 3.

B. Final Construction of Plasmid pBLcat

About 88 µg of plasmid pBKneo1 DNA in 50 µl of TE buffer were added to 7.5 µl of 10X AccI buffer, 30 µl of H₂O, and 15 µl (about 75 units) of restriction enzyme AccI, and the resulting reaction was incubated at 37° C. for 2 hours. The AccI-digested BK virus DNA was loaded on an agarose gel, and the ~1.4 kb fragment that contains the BK enhancer was separated from the other digestion products. The ~1.4 kb AccI restriction fragment was then isolated in substantial accordance with the procedure described in Example 4A. About 5 µg of the fragment were resuspended in 5 µl of 10X PvuII buffer, 45 µl of H₂O, and 5 µl (about 25 units) of restriction enzyme PvuII, and the resulting reaction was incubated at 37° C. for 2 hours. The PvuII-digested DNA was then isolated and prepared for ligation in substantial accordance with the procedure of Example 4A. About 2 µg of the desired ~1.28 kb AccI-PvuII fragment were obtained and dissolved in 5 µl of TE buffer.

About 1 µg of plasmid pLPcat DNA was dissolved in 5 µl of 10X AccI buffer and 40 µl of H₂O. About 5 µl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 µl of 10X StuI buffer, 40 µl of H₂O, and 5 µl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 µg of the desired ~4.81 kb restriction fragment was obtained and dissolved in 20 µl of TE buffer.

Figure 6:
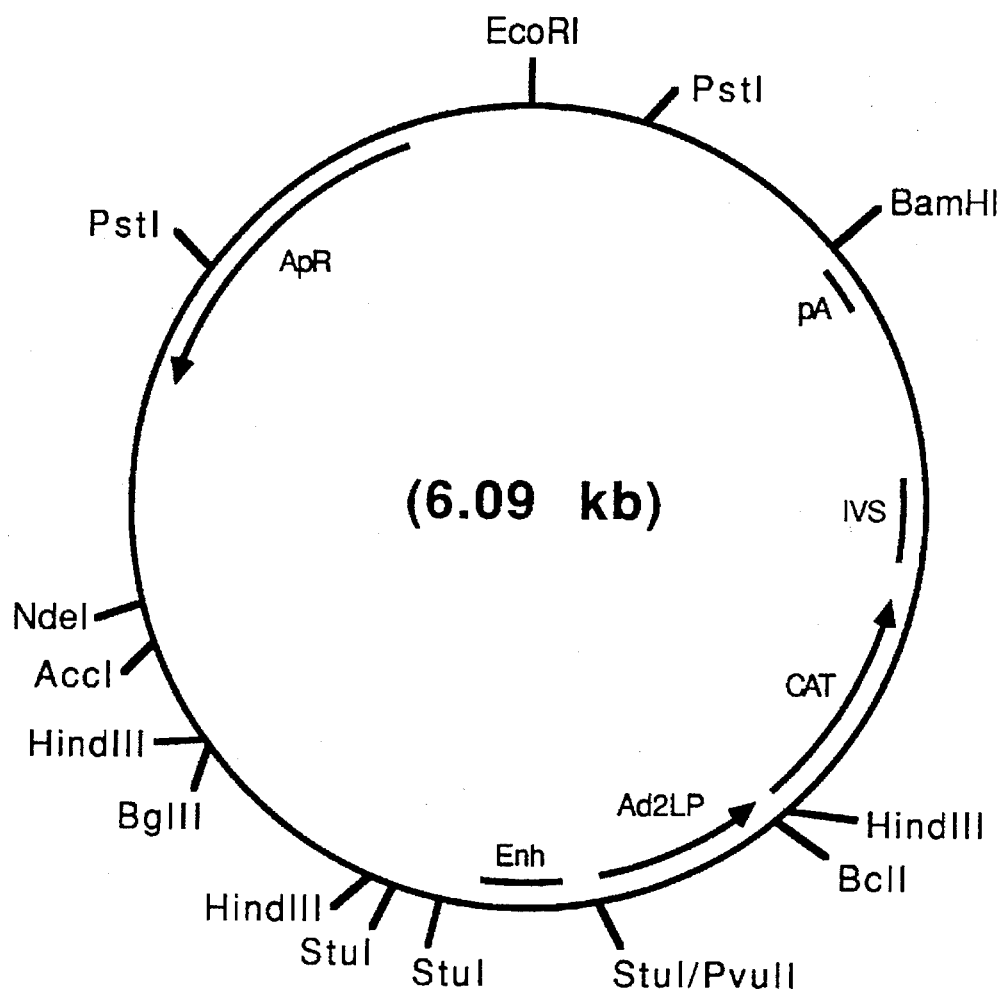
FIG. 6 is a restriction site and function map of plasmid pBLcat.
Figure 7:
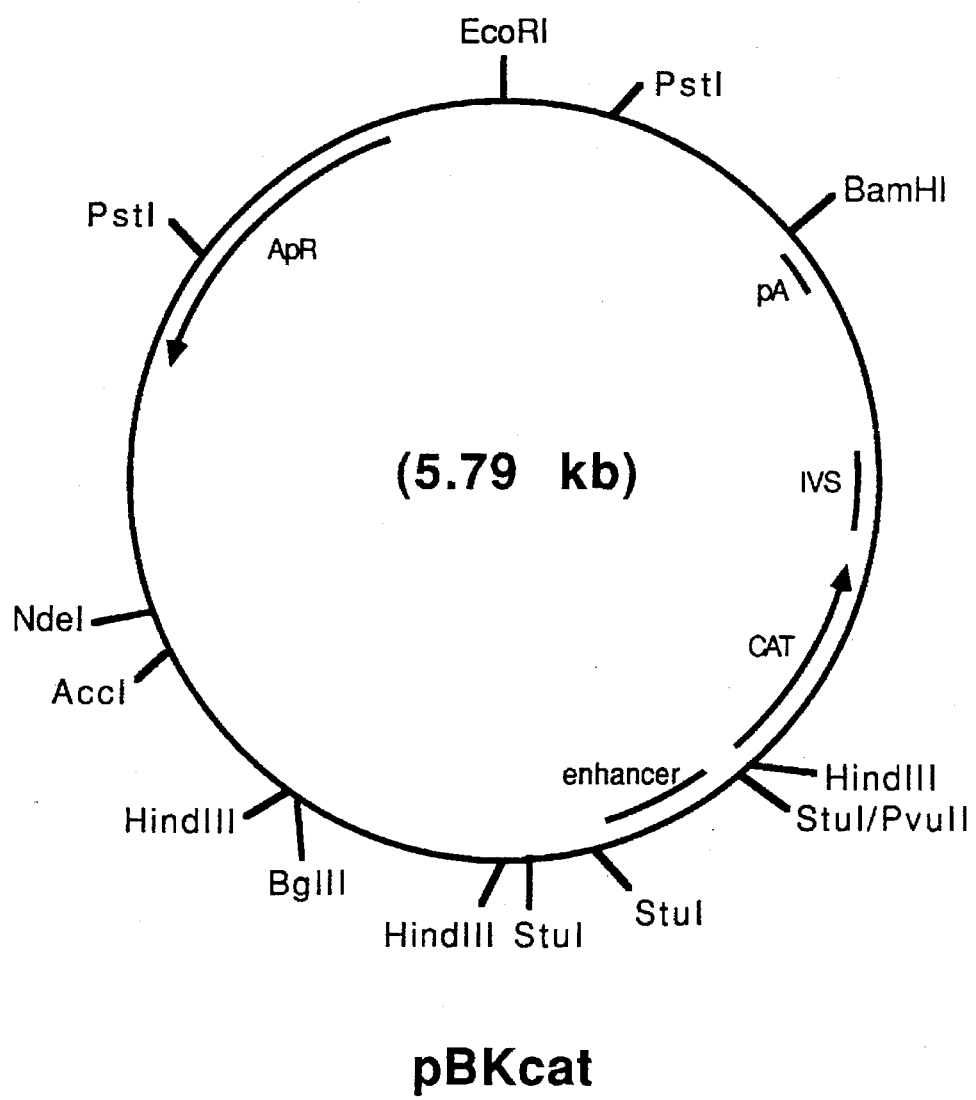
FIG. 7 is a restriction site and function map of plasmid pBKcat.

The 5 µl of ~4.81 kb AccI-StuI restriction fragment of plasmid pLPcat were added to 5 µl of ~1.28 kb AccI-PvuII restriction fragment of BK virus. After the addition of 3 µl of 10X ligase buffer, 15 µl of H₂O, and 2 µl (about 1000 units) of T4 DNA ligase to the mixture of DNA, the resulting ligation reaction was incubated at 16° C. overnight. The ligated DNA constituted the desired plasmid pBLcat. A restriction site and function map of plasmid pBLcat is presented in FIG. 6 of the accompanying drawings.

The ligated DNA was used to transform *E. coli* K12 HB101 cells in substantial accordance with the procedure described in Example 3. *E. coli* K12 HB101/pBLcat transformants were identified by restriction enzyme analysis of their plasmid DNA. Plasmid pBLcat DNA was prepared for use in subsequent constructions in substantial accordance with the procedure of Example 3.

EXAMPLE 5

Construction of Plasmid pSBLcat

About 100 µg of plasmid pBLcat DNA were dissolved in 10 µl of 10X HindIII buffer (0.5M NaCl; 0.1M Tris-HCl, pH=8.0; 0.1M MgCl₂; and 1 mg/ml BSA) and 80 µl of H₂O. About 10 µl (about 100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was well separated from the other digestion products; then, the ~0.87 kb fragment was isolated and prepared for ligation in substantial accordance with the procedure of Example 4A. About 10 µg of the desired fragment were obtained and dissolved in 50 µl of TE buffer.

About 1 µg of plasmid pSV2cat DNA in 1 µl of TE buffer was dissolved in 2 µl of 10X HindIII buffer and 16 µl of H₂O. About 1 µl (about 10 units) of restriction enzyme HindIII was added to the solution of DNA, and the resulting reaction was incubated at 37° C. for 2 hours. The reaction was stopped by extracting the reaction mixture first with phenol, then twice with chloroform. The HindIII-digested plasmid pSV2cat DNA was precipitated with ethanol and resuspended in 100 µl of TE buffer. The HindIII-digested plasmid pSV2cat DNA was treated with calf-intestinal alkaline phosphatase in substantial accordance with the procedure of Example 2 and then resuspended in 10 µl of TE buffer.

Figure 8:
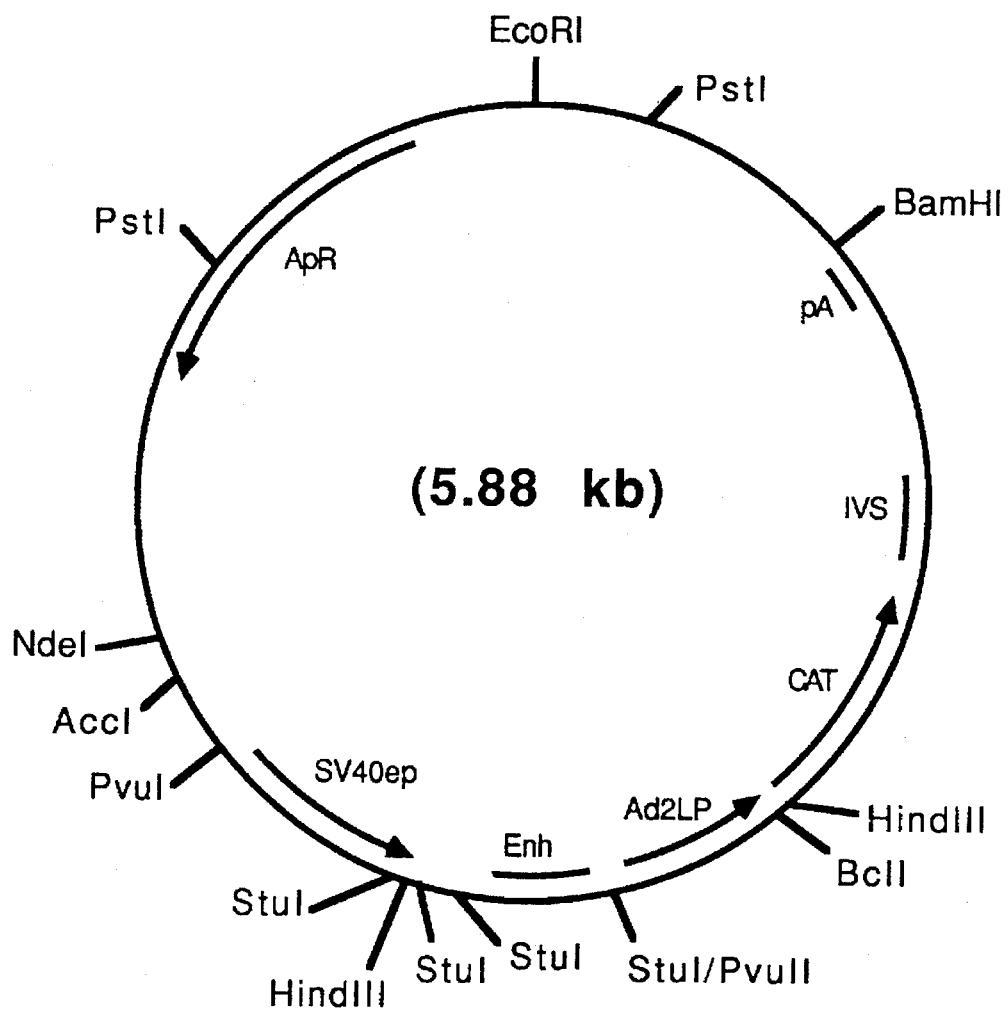
FIG. 8 is a restriction site and function map of plasmid pSBLcat.

About 5 µl of the ~0.87 kb HindIII restriction fragment of plasmid pBLcat were added to the 10 µl of HindIII-digested plasmid pSV2cat, and then, 3 µl of 10X ligase buffer, 2 µl (about 1000 units) of T4 DNA ligase, and 13 µl of H₂O were added to the solution of DNA, and the resulting reaction was incubated at 16° C. for 2 hours. The ligated DNA constituted the desired plasmid pSBLcat. The ligated DNA was used to transform *E. coli* K12 HB101 in substantial accordance with the procedure of Example 2. The transformed cells were plated on L agar containing ampicillin, and the plasmid DNA of the ampicillin-resistant transformants was examined by restriction enzyme analysis to identify the *E. coli* K12 HB101/pSBLcat transformants. The ~0.87 kb HindIII restriction fragment that encodes the BK enhancer and Ad2 late promoter could insert into HindIII-digested plasmid pSBLcat in one of two orientations, only one of which yields plasmid pSBLcat. A restriction site and function map of plasmid pSBLcat is presented in FIG. 8 of the accompanying drawings.

EXAMPLE 6

Construction of Plasmid pLPC

About 20 µg of plasmid pBLcat DNA were dissolved in 10 µl of 10X HindIII buffer and 80 µl of H₂O. About 10 µl (~100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was separated from the other digestion products; then, the ~0.87 kb fragment was isolated and prepared for ligation in substantial accordance with the procedure of Example 4A. About 2 µg of the desired fragment were obtained and dissolved in 5 µl of TE buffer.

Figure 9:
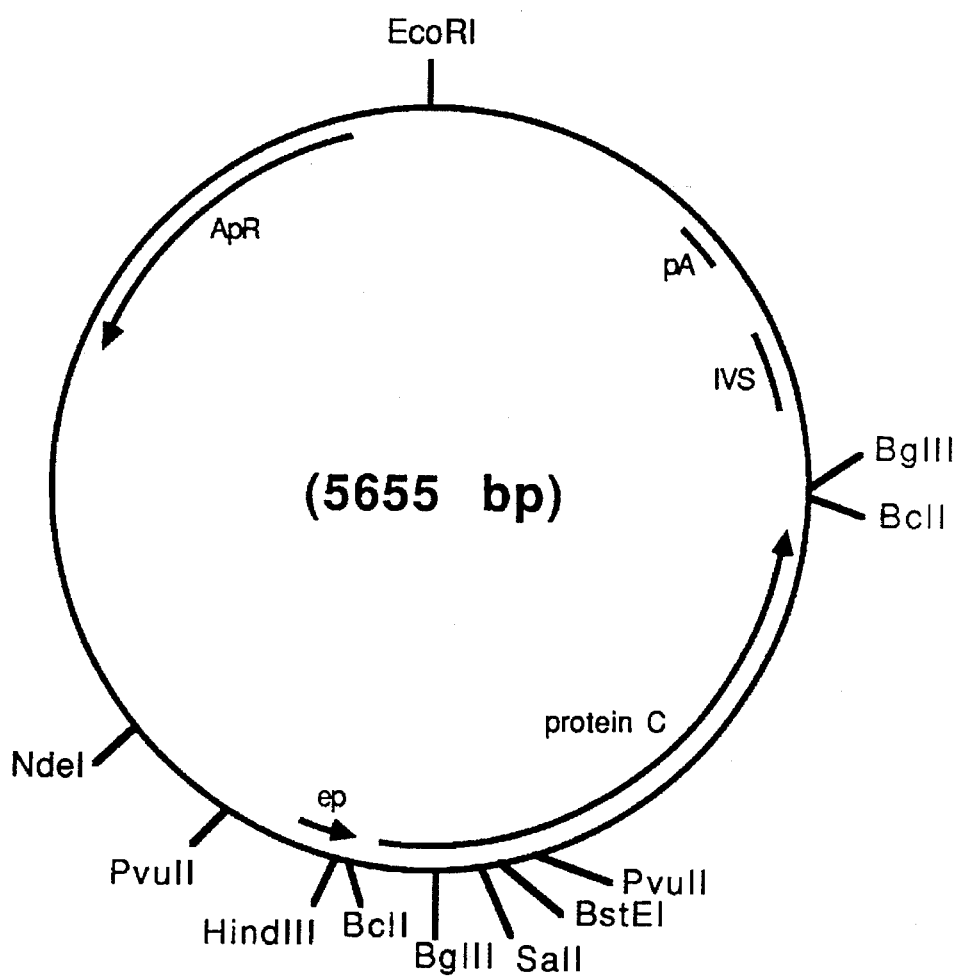
FIG. 9 is a restriction site and function map of plasmid pL133.

Plasmid pL133 contains the entire cDNA coding sequence for the zymogen form of human protein C. Plasmid pL133 is disclosed and claimed in Bang et al., U.S. Pat. No. 4,775,624, issued Oct. 4, 1988, the entire teaching of which is herein incorporated by reference. A restriction site and function map of plasmid pL133 is presented in FIG. 9 of the accompanying drawings.

About 1.5 µg of plasmid pL133 DNA was dissolved in 2 µl of 10X HindIII buffer and 16 µl of H$_2$O. About 1 µl (~10 units) of restriction enzyme HindIII was added to the solution of DNA, and the resulting reaction was incubated at 37° C. for 2 hours. The DNA was then diluted to 100 µl with TE buffer and treated with calf-intestinal alkaline phosphatase in substantial accordance with the procedure in Example 2. The HindIII-digested plasmid pL133 DNA was extracted twice with phenol and once with chloroform, precipitated with ethanol, and resuspended in 10 µl of TE buffer.

Figure 10:
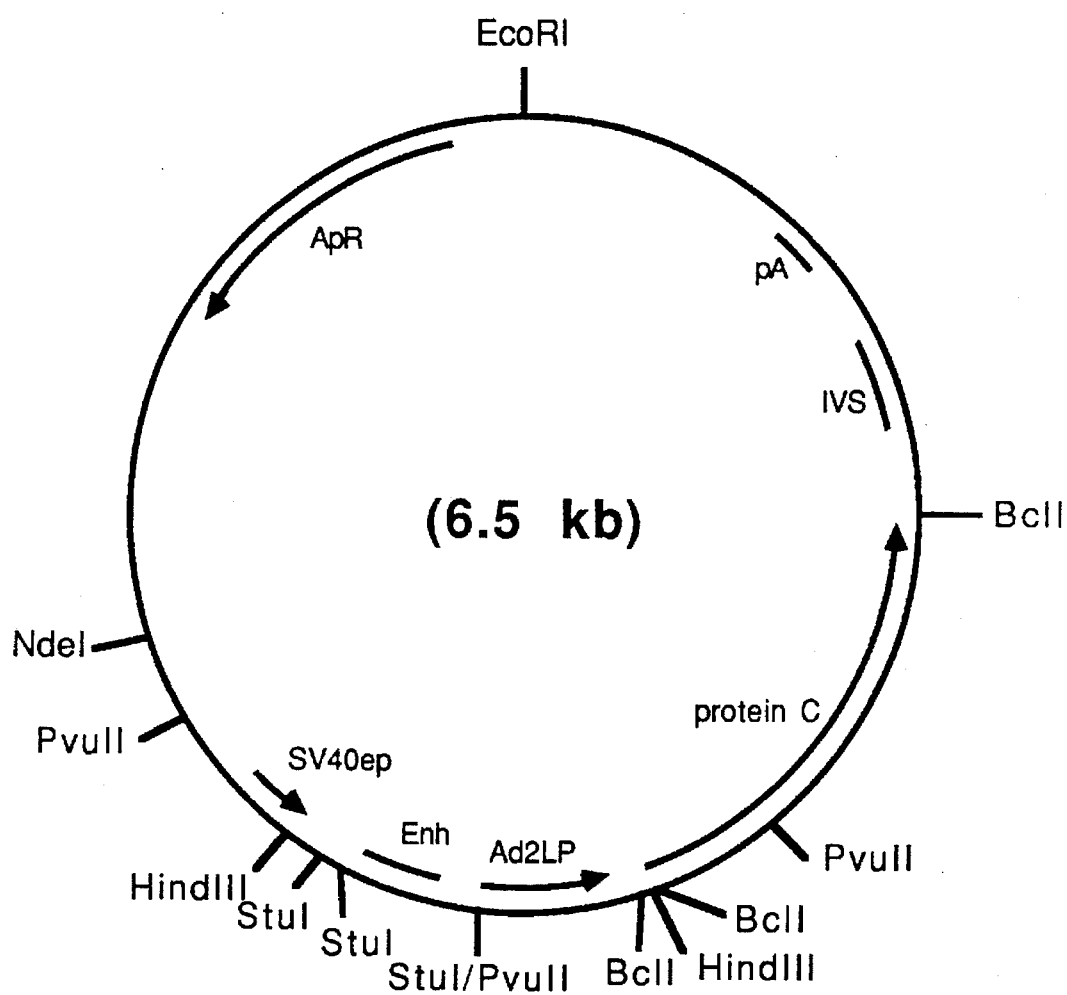
FIG. 10 is a restriction site and function map of plasmid pLPC.

About 5 µl of the ~0.87 kb HindIII restriction fragment of plasmid pBLcat were added to the 1.5 µl of HindIII-digested plasmid pL133, and then, 1 µl of 10X ligase buffer, 1 µl (~1000 units) of T4 DNA ligase, and 1.5 µl of H$_2$O were added to the solution of DNA, and the resulting reaction was incubated at 16° C. overnight. The ligated DNA constituted the desired plasmid pLPC. A restriction site and function map of plasmid pLPC is presented in FIG. 10 of the accompanying drawings.

The ligated DNA was used to transform *E. coli* K12 HB101 in substantial accordance with the procedure of Example 3. The transformed cells were plated on L agar containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only one of which yields plasmid pLPC.

EXAMPLE 7

Construction of Plasmids pLPC4 and pLPC5

About 1 µg (1 µl) of the BK virus DNA prepared in Example 1 and 1 µg of plasmid pLPC (1 µl) were dissolved in 2 µl of 10X EcoRI buffer and 14 µl) were About 2 µl (~10 units) of restriction enzyme EcoRI of H$_2$O. added to the solution of DNA, and the resulting reaction was incubated at 37° C. for 2 hours. The EcoRI-digested mixture of BK virus and plasmid pLPC DNA was extracted once with buffered phenol and once with chloroform. Then, the DNA was collected by adjusting the NaCl concentration to 0.25M, adding two volumes of ethanol, incubating the solution in a dry ice-ethanol bath for 2 minutes, and centrifuging the solution to pellet the DNA. The supernatant was discarded, and the DNA pellet was rinsed with 70% ethanol, dried, and resuspended in 12 µl of TE buffer.

Figure 11:
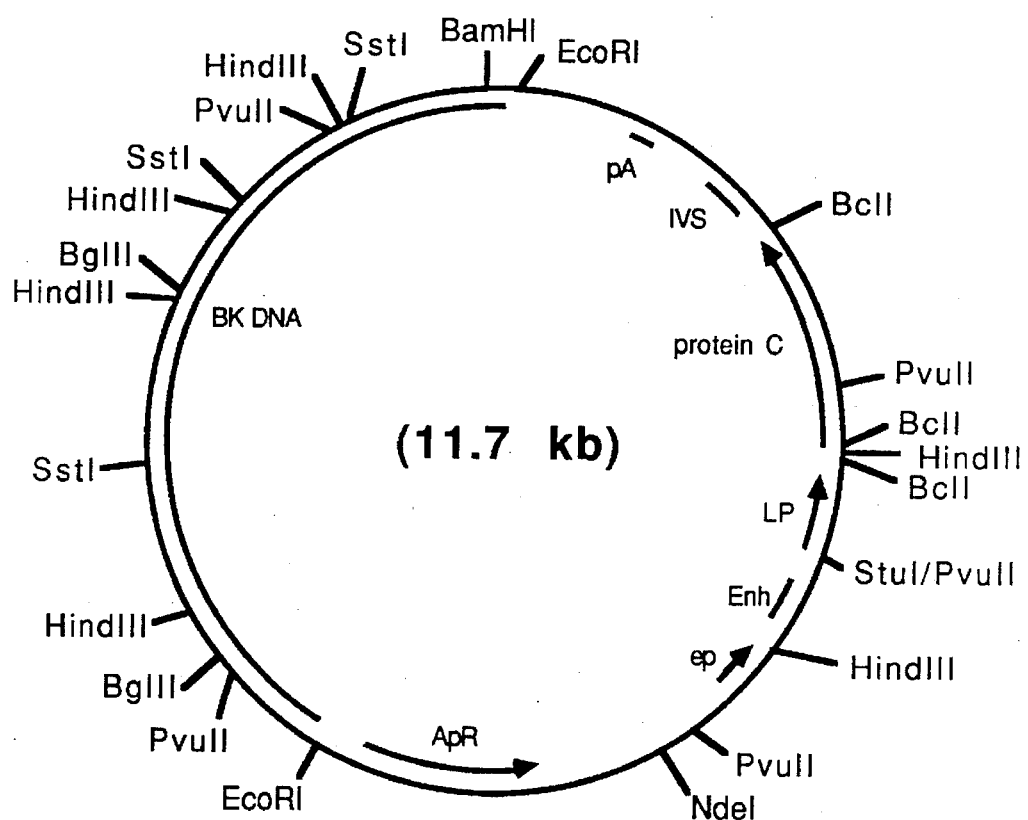
FIG. 11 is a restriction site and function map of plasmid pLPC4.

About 13 µl of H$_2$O and 3 µl of 10X ligase buffer were added to the EcoRI-digested mixture of BK virus and plasmid pLPC DNA. Two µl (~1000 units) of T4 DNA ligase were added to the solution of DNA, and the resulting reaction was incubated at 16° C. for 2 hours. The ligated DNA constituted the desired plasmids pLPC4 and pLPC5, which differ only with respect to the orientation of the inserted BK virus DNA. A restriction site and function map of plasmid pLPC4 is presented in FIG. 11 of the accompanying drawings.

The ligated DNA constituted the desired plasmids pLPC4 and pLPC5 and was used to transform *E. coli* K12 EB101 competent cells in substantial accordance with the procedure of Example 2. The transformed cells were plated on L agar containing 100 µg/ml ampicillin. The *E. coli* K12 HB101/pLPC4 and *E. coli* K12 HB101/pLPC5 transformants were identified by their ampicillin-resistant phenotype and by restriction enzyme analysis of their plasmid DNA.

EXAMPLE 8

Construction of Plasmids pLPChyg1 and pLPChyg2

Figure 12:
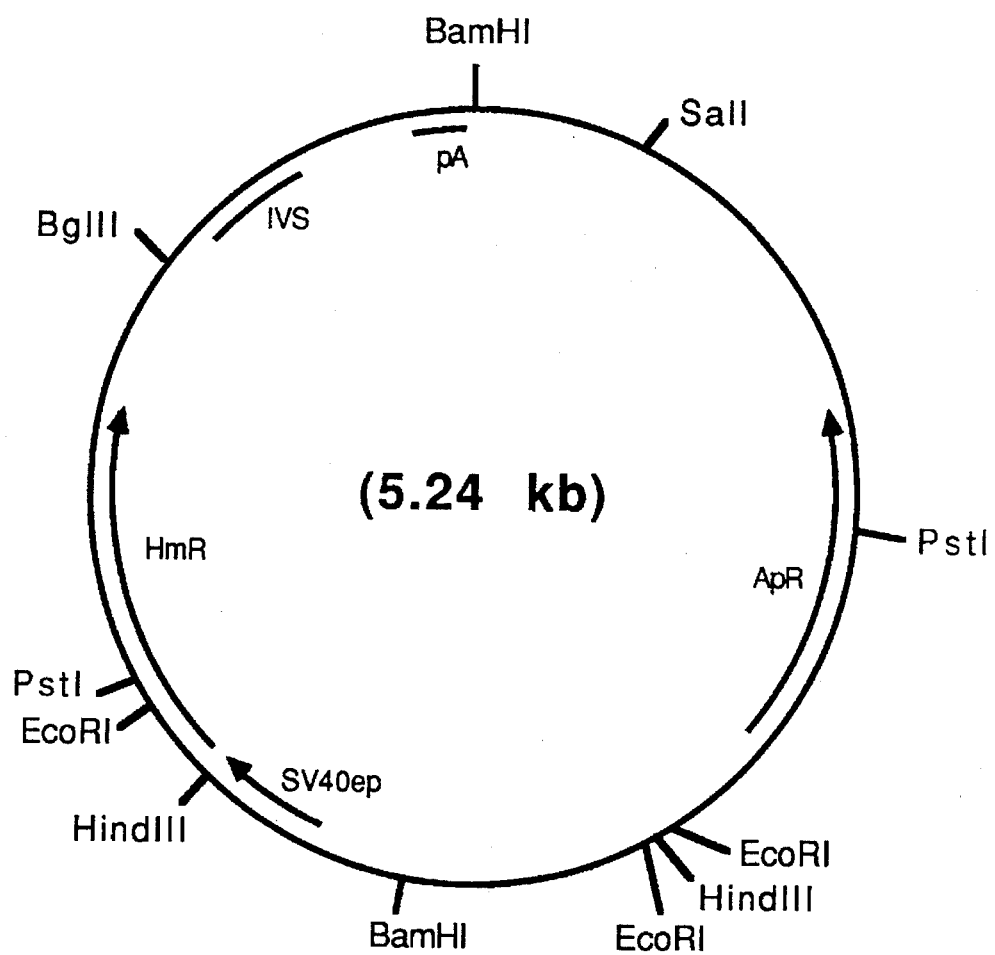
FIG. 12 is a restriction site and function map of plasmid pSV2hyg.

*E. coli* K12 RR1/pSV2hyg cells are obtained from the Northern Regional Research Laboratory under the accession number NRRL B-18039. Plasmid pSV2hyg DNA is obtained from the cells in substantial accordance with the procedure of Example 3. A restriction site and function map of plasmid pSV2hyg is presented in FIG. 12 of the accompanying drawings.

About 10 µg (in 10 µl of TE buffer) of plasmid pSV2hyg were added to 2 µl of 10X BamHI buffer and 6 µl of H$_2$O. About 2 µl (about 20 units) of restriction enzyme BamHI were added to the solution of DNA, and the resulting reaction was incubated at 37° C. for 2 hours. The reaction was extracted first with phenol and then was extracted twice with chloroform. The BamHI-digested plasmid pSV2hyg DNA was loaded onto an agarose gel, and the hygromycin resistance gene-containing, ~2.5 kb restriction fragment was isolated in substantial accordance with the procedure described in Example 4A.

About 5 µl of 10X Klenow buffer (0.2 mM in each of the four dNTPs; 0.5M Tris-HCl, pH=7.8; 50 mM MgCl$_2$; 0.1M 2-mercaptoethanol; and 100 µg/ml BSA) and 35 µl of H$_2$O were added to the solution of BamHI-digested plasmid pSV2hyg DNA, and then, about 25 units of Klenow enzyme (about 5 µl, as marketed by BRL) were added to the mixture of DNA, and the resulting reaction was incubated at 16° C. for 30 minutes. The Klenow-treated, BamHI-digested plasmid pSV2hyg DNA was extracted once with phenol and once with chloroform and then precipitated with ethanol. About 2 µg of the desired fragment were obtained and suspended in 5 µl of TE buffer.

About 10 µg (10 µl) of plasmid pLPC DNA were added to 2 µl of 10X StuI buffer and 6 µl of H$_2$O. About 2 µl (~10 units) of restriction enzyme StuI were added to the solution of DNA, and the resulting reaction was incubated at 37° C. for 2 hours. The StuI-digested plasmid pLPC DNA was precipitated with ethanol, collected by centrifugation, and resuspended in 2 µl of 10X NdeI buffer (1.5M NaCl; 0.1M Tris-HCl, pH=7.8; 70 mM MgCl$_2$; 60 mM 2-mercaptoethanol; and 1 mg/ml BSA) and 16 µl of H$_2$O. About 2 µl (~10 units) of restriction enzyme NdeI were added to the solution of StuI-digested DNA, and the resulting reaction was incubated at 37° C. for 2 hours.

The NdeI-StuI-digested plasmid pLPC DNA was precipitated with ethanol, collected by centrifugation, and resuspended in 5 μl of 10X Klenow buffer and 40 μl of H₂O. About 5 μl (~25 units) of Klenow enzyme were added to the solution of DNA, and the resulting reaction was incubated at 16° C. for 30 minutes. After the Klenow reaction, the reaction mixture was loaded onto an agarose gel, and the ~5.82 kb NdeI-StuI restriction fragment was isolated from the gel. About 5 μg of the desired fragment were obtained and suspended in 5 μl of TE buffer.

Figure 13:
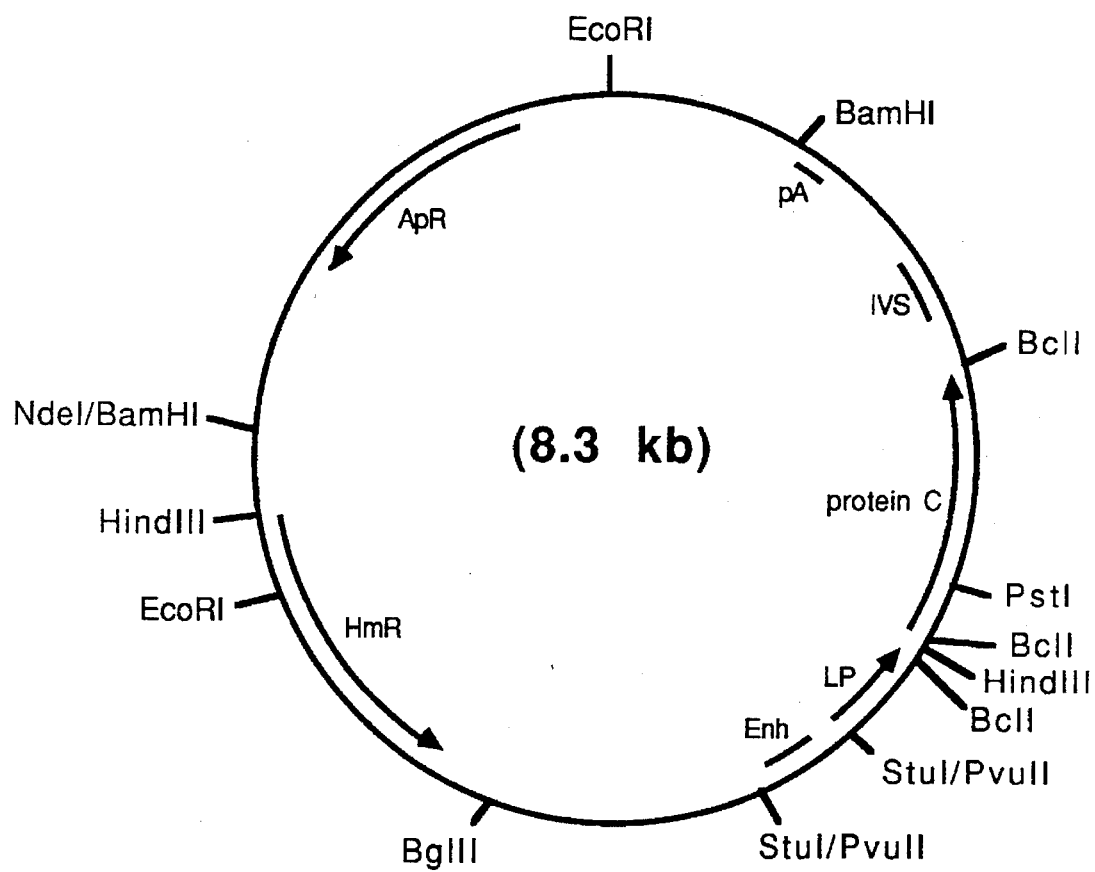
FIG. 13 is a restriction site and function map of plasmid pLPChyg1.

About 2 μl of the ~2.5 kb Klenow-treated BamHI restriction fragment of plasmid pSV2hyg were mixed with about 1 μl of the ~5.82 kb Klenow-treated NdeI-StuI restriction fragment of plasmid pLPC, and about 3 μl of 10X ligase buffer, 2 μl of T4 DNA ligase (~1000 units), 1 μl of T4 RNA ligase (~1 unit), and 14 μl of H₂O were added to the solution of DNA. The resulting reaction was incubated at 16° C. overnight. The ligated DNA constituted the desired plasmids pLPChyg1 and pLPChyg2, which differ only with respect to the orientation of the ~2.5 kb Klenow-treated, BamHI restriction fragment of plasmid pSV2hyg. A restriction site and function map of plasmid pLPChyg1 is presented in FIG. 13 of the accompanying drawings. The ligated DNA was used to transform *E. coli* K12 HB101 in substantial accordance with the procedure of Example 3. The desired *E. coli* K12 HB101/pLPChyg1 and *E. coli* K12 HB101/pLPChyg2 transformants were plated on L agar containing ampicillin and identified by restriction enzyme analysis of their plasmid DNA.

EXAMPLE 9

Construction of Plasmid pBW32

A. Construction of Intermediate Plasmid pTPA103

Plasmid pTPA102 comprises the coding sequence of human tissue plasminogen activator (TPA). Plasmid pTPA102 can be isolated from *E. coli* K12 MM294/pTPA102, a strain available from the Northern Regional Research Laboratory under the accession number NRRL B-15834. Plasmid pTPA102 DNA is isolated from *E. coli* K12 MM294/pTPA102 in substantial accordance with the procedure of Example 3.

About 50 μg of plasmid pTPA102 (in about 50 μl of TE buffer) were added to 10 μl of 10X Tth111I buffer (0.5M NaCl; 80 mM Tris-HCl, pH=7.4; 80 mM MgCl₂; 80 mM 2-mercaptoethanol; and 1 mg/ml BSA) and 80 μl of H₂O. About 10 μl (~50 units) of restriction enzyme Tth111I were added to the solution of DNA, and the resulting reaction was incubated at 65° C. for 2 hours. The reaction mixture was loaded onto an agarose gel, and the ~4.4 kb Tth111I restriction fragment that comprises the TPA coding sequence was isolated from the gel. The other digestion products, 3.1 kb and 0.5 kb restriction fragments, were discarded. About 10 μg of the desired ~4.4 kb Tth111I restriction fragment were obtained and suspended in 10 μl of TE buffer.

About 5 μl of 10X Klenow buffer and 30 μl of H₂O were added to the solution comprising the ~4.4 kb Tth111I restriction fragment, and after the further addition of about 5 μl of Klenow enzyme (~5 units), the reaction mixture was incubated at 16° C. for 30 minutes. After the Klenow reaction, the DNA was precipitated with ethanol and resuspended in 3 μl of 10X ligase buffer and 14 μl of H₂O.

BamHI linkers (New England Biolabs), which had the following sequence:

```
5'-CGGATCCG-3'
   ||||||||
3'-GCCTAGGC-5',
``` were kinased and prepared for ligation by the following procedure. Four μl of linkers (~2 μg) were dissolved in 20.15 μl of H₂O and 5 μl of 10X kinase buffer (500 mM Tris-HCl, pH=7.6 and 100 mM MgCl₂), incubated at 90° C. for two minutes, and then cooled to room temperature. Five μl of γ-³²P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01M ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb Tth111I restriction fragment, and after the addition of 2 μl of T4 DNA ligase (~1000 units) and 1 μl of T4 RNA ligase (~2 units), the ligation reaction was incubated overnight at 4° C. The ligated DNA was precipitated with ethanol and resuspended in 5 μl of 10X HindIII buffer and 40 μl of H₂O. About 5 μl (~50 units) of restriction enzyme HindIII were added to the solution of DNA, and the resulting reaction was incubated at 37° C. for 2 hours.

The HindIII-digested DNA was precipitated with ethanol and resuspended in 10 μl of 10X BamHI buffer and 90 μl of H₂O. About 10 μl (~100 units) of restriction enzyme BamHI were added to the solution of DNA, and the resulting reaction was incubated at 37° C. for 2 hours. After the BamHI digestion, the reaction mixture was loaded onto an agarose gel, and the ~2.0 kb BamHI-HindIII restriction fragment was isolated from the gel. About 4 μg of the desired fragment were obtained and suspended in about 5 μl of TE buffer.

To construct plasmid pTPA103, the ~2.0 kb BamHI-HindIII restriction fragment derived from plasmid pTPA102 was inserted into BamHI-HindIII-digested plasmid pRC. Plasmid pRC was constructed by inserting an ~288 bp EcoRI-ClaI restriction fragment that comprises the promoter and operator (trpPO) sequences of the *E. coli* trp operon into EcoRI-ClaI-digested plasmid pKC7. Plasmid pKC7 can be obtained from the American Type Culture Collection in *E. coli* K12 N100/pKC7 under the accession number ATCC 37084. The ~288 bp EcoRI-ClaI restriction fragment that comprises the trpPO can be isolated from plasmid pTPA102, which can be isolated from *E. coli* K12 MM294/pTPA102 (NRRL B-15834). Plasmid pKC7 and plasmid pTPA102 DNA can be obtained from the aforementioned cell lines in substantial accordance with the procedure of Example 3. This ~0.29 kb EcoRI-ClaI restriction fragment of plasmid pTPA102 comprises the transcription activating sequence and most of the translation activating sequence of the *E. coli* trp gene and has the sequence depicted below:

```
         10         20         30         40         50
5'-AATTCACGCT GTGGTGTTAT GGTCGGTGGT CGCTAGGGTG CCGACGCGCA
   |||||| |||||||||| |||||||||| |||||||||| ||||||||||
3'-GTGCGA CACCACAATA CCAGCCACCA GCGATCCCAC GGCTGCGCGT
```

-continued

```
         60         70         80         90        100
TCTCGACTGC ACGGTGCACC AATGCTTCTG GCGTCAGGCA GCCAATCGGA
|||||||||| |||||||||| |||||||||| |||||||||| ||||||||||
AGAGCTGACG TGCCACGTGG TTACGAAGAC CGCAGTCCGT CGGTTAGCCT 110        120        130        140        150
AGCTGTGGTA TGGCTGTGCA GGTCGTATAA TCACCGCATA ATTCGAGTCG
|||||||||| |||||||||| |||||||||| |||||||||| ||||||||||
TCGACACCAT ACCGACACGT CCAGCATATT AGTGGCGTAT TAAGCTCAGC 160        170        180        190        200
CTCAAGGCGC ACTCCCGTTC CGGATAATGT TTTTTGCTCC GACATCATAA
|||||||||| |||||||||| |||||||||| |||||||||| ||||||||||
GAGTTCCGCG TGAGGGCAAG GCCTATTACA AAAAACGAGG CTGTAGTATT 210        220        230        240        250
CGGTTCCGGC AAATATTCTG AAATGAGCTG TTGACAATTA ATCATCGAAC
|||||||||| |||||||||| |||||||||| |||||||||| ||||||||||
GCCAAGGCCG TTTATAAGAC TTTACTCGAC AACTGTTAAT TAGTAGCTTG 260        270        280     287
TAGTTAACTA GTACGCAAGT TCTCGTAAAA AGGGTAT-3'
|||||||||| |||||||||| |||||||||| |||||||
ATCAATTGAT CATGCGTTCA AGAGCATTTT TCCCATAGC-5'
```

Thus, to construct plasmid pRC, about 2 μg of plasmid pKC7 in 10 μl of TE buffer were added to 2 μl of 10X ClaI buffer (0.5M NaCl; 60 mM Tris-HCl, pH=7.9, 60 mM MgCl$_2$; and 1 mg/ml BSA) and 6 μl of H$_2$O. About 2 μl (~10 units) of restriction enzyme ClaI were added to the solution of plasmid pKC7 DNA, and the resulting reaction was incubated at 37° C. for 2 hours. The ClaI-digested plasmid pKC7 DNA was precipitated with ethanol and resuspended in 2 μl of 10X EcoRI buffer and 16 μl of H$_2$O. About 2 μl (~10 units) of restriction enzyme EcoRI were added to the solution of ClaI-digested plasmid pKC7 DNA, and the resulting reaction was incubated at 37° C. for 2 hours.

The EcoRI-ClaI-digested plasmid pKC7 DNA was extracted once with phenol and then twice with chloroform. The DNA was then precipitated with ethanol and resuspended in 3 μl of 10X ligase buffer and 20 μl of H$_2$O. A restriction site and function map of plasmid pKC7 can be obtained from Maniatis et al., *Molecular Cloning* (Cold Spring Harbor Laboratory, 1982), page 8.

About 20 μg of plasmid pTPA102 in about 20 μl of TE buffer were added to 10 μl of 10X ClaI buffer and 60 μl of H$_2$O. About 10 μl (~50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 μl of 10X EcoRI buffer and 80 μl of H$_2$O. About 10 μl (~50 units) of restriction enzyme EcoRI were added to the solution of ClaI-digested plasmid pTPA102 DNA, and the resulting reaction was incubated at 37° C. for 2 hours.

The EcoRI-ClaI-digested plasmid pTPA102 DNA was extracted once with phenol, loaded onto a 7% polyacrylamide gel, and electrophoresed until the ~288 bp EcoRI-ClaI restriction fragment that comprises the trpPO was separated from the other digestion products. The ~288 bp EcoRI-ClaI restriction fragment was isolated from the gel; about 1 μg of the desired fragment was obtained, suspended in 5 μl of TE buffer, and added to the solution of EcoRI-ClaI-digested plasmid pKC7 DNA prepared as described above. About 2 μl (~1000 units) of T4 DNA ligase were then added to the mixture of DNA, and the resulting ligation reaction was incubated at 16° C. for 2 hours. The ligated DNA constituted the desired plasmid pRC DNA.

The ligated DNA was used to transform *E. coli* K12 HB101 competent cells in substantial accordance with the procedure of Example 2. The transformed cells were plated on L agar containing 100 μg/ml ampicillin, and the ampicillin-resistant transformants were screened by restriction enzyme analysis of their plasmid DNA to identify the desired *E. coli* K12 HB101/pRC colonies. Plasmid pRC DNA was obtained from the *E. coli* K12 HB101/pRC transformants in substantial accordance with the procedure of Example 3.

About 2 μg of plasmid pRC DNA in 2 μl of TE buffer were added to 2 μl of 10X HindIII buffer and 16 μl of H$_2$O. About 2 μl (~10 units) of restriction enzyme HindIII were added to the solution of plasmid pRC DNA, and the resulting reaction was incubated at 37° C. for two hours. The HindIII-digested plasmid pRC DNA was precipitated with ethanol and resuspended in 2 μl of 10X BamHI buffer and 16 μl of H$_2$O. About 2 μl (~10 units) of restriction enzyme BamHI were added to the solution of HindIII-digested plasmid pRC DNA, and the resulting reaction was incubated at 37° C. for 2 hours.

The BamHI-HindIII-digested plasmid pRC DNA was extracted once with phenol and then twice with chloroform. The DNA was precipitated with ethanol and resuspended in 3 μl of 10X ligase buffer and 20 μl of H$_2$O. The ~4 μg (in ~5 μl of TE buffer) of ~2.0 kb HindIII-BamHI restriction fragment of plasmid pTPA102 were then added to the solution of BamHI-HindIII-digested plasmid pRC DNA. About 2 μl (~1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms *E. coli* at a lower frequency than closed, circular DNA. To digest the ligated DNA, the DNA was first precipitated with ethanol and then resuspended in 2 μl of 10X NcoI buffer (1.5M NaCl; 60 mM Tris-HCl, pH=7.8; 60 mM MgCl$_2$; and 1 mg/ml BSA) and 16 μl of H$_2$O. About 2 μl (~10 units) of restriction enzyme NcoI were added to the solution of DNA, and the resulting reaction was incubated at 37° C. for 2 hours.

The ligated and then NcoI-digested DNA was used to transform *E. coli* K12 RV308 (NRRL B-1562). *E. coli* K12 RV308 cells were made competent and transformed in substantial accordance with the procedure of Example 3. The transformation mixture was plated on L agar containing 100 μg/ml ampicillin. The ampicillin-resistant transformants were tested for sensitivity to kanamycin, for though plasmid pRC confers kanamycin resistance, plasmid pTPA103 does not. The ampicillin-resistant, kanamycin-sensitive transformants were then used to prepare plasmid DNA, and the plasmid DNA was examined by restriction enzyme analysis to identify the E. coli K12 RV308/pTPA103 transformants. Plasmid pTPA103 DNA was isolated from the E. coli K12 RV308/pTPA103 cells in substantial accordance with the procedure of Example 3.

B. Construction of Intermediate Plasmid pBW25

About 1 μg of plasmid pTPA103 DNA in 1 μl of TE buffer was added to 2 μl of 10X BglII buffer and 16 μl of H₂O. About 1 μl (~5 units) of restriction enzyme BglII was added to the solution of plasmid pTPA103 DNA, and the resulting reaction was incubated at 37° C. for 2 hours. The BglII-digested plasmid pTPA103 DNA was precipitated with ethanol and resuspended in 5 μl of 10X Klenow buffer and 44 μl of H₂O. About 1 μl of Klenow enzyme (~1 unit) was added to the solution of BglII-digested plasmid pTPA103 DNA, and the resulting reaction was incubated at 16° C. for 2 hours. The Klenow-treated, BglII-digested plasmid pTPA103 DNA was precipitated with ethanol and resuspended in 3 μl of 10X ligase buffer and 22 μl of H₂O.

About 2 μl (0.2 μg) of unkinased NdeI linkers (New England Biolabs) of sequence:

were added to the solution of Klenow-treated, BglII-digested plasmid pTPA103 DNA, together with 2 μl (~1000 units) of T4 DNA ligase and 1 μl (~2 units) of T4 RNA ligase, and the resulting ligation reaction was incubated at 4° C. overnight. The ligated DNA constituted plasmid pTPA103derNdeI, which is substantially similar to plasmid pTPA103, except plasmid pTPA103derNdeI has an NdeI recognition sequence where plasmid pTPA103 has a BglII recognition sequence.

The ligated DNA was used to transform E. coli K12 RV308 competent cells in substantial accordance with the procedure described in Example 2. The transformed cells were plated on L-agar containing ampicillin, and the E. coli K12 RV308/pTPA103derNdeI transformants were identified by restriction enzyme analysis of their plasmid DNA. Plasmid pTPA103derNdeI DNA was isolated from the transformants for use in subsequent constructions in substantial accordance with the procedure of Example 3.

About 10 μg of plasmid pTPA103derNdeI DNA in 10 μl of TE buffer were added to 2 μl of 10X AvaII buffer (0.6M NaCl; 60 mM Tris-HCl, pH=8.0; 0.1M MgCl₂; 60 mM 2-mercaptoethanol; and 1 mg/ml BSA) and 6 μl of H₂O. About 2 μl (~10 units) of restriction enzyme AvaII were added to the DNA, and the resulting reaction was incubated at 37° C. for 2 hours. The AvaII-digested DNA was loaded onto an agarose gel and electrophoresed until the ~1.4 kb restriction fragment was separated from the other digestion products. The ~1.4 kb AvaII restriction fragment of plasmid pTPA103derNdeI was isolated from the gel; about 2 μg of the desired fragment were obtained and suspended in 5 μl of TE buffer.

About 5 μl of 10X Klenow buffer, 35 μl of H₂O, and 5 μl (~5 units) of Klenow enzyme were added to the solution of ~1.4 kb AvaII restriction fragment, and the resulting reaction was incubated at 16° C. for thirty minutes. The Klenow-treated DNA was precipitated with ethanol and resuspended in 3 μl of 10X ligase buffer and 14 μl of H₂O.

About 2 μg of HpaI linkers of sequence:

were kinased in substantial accordance with the procedure of Example 10A. About 10 μl of the kinased linkers were added to the solution of Klenow-treated, ~1.4 kb AvaII restriction fragment of plasmid pTPA103derNdeI together with 2 μl (~1000 units) of T4 DNA ligase and 1 μl (~1 unit) of T4 RNA ligase, and the resulting reaction was incubated at 16° C. overnight.

The ligated DNA was extracted once with phenol, extracted twice with chloroform, precipitated with ethanol, and resuspended in 2 μl of 10X EcoRI buffer and 16 μl of H₂O. About 2 μl (~10 units) of restriction enzyme EcoRI were added to the solution of DNA, and the resulting reaction was incubated at 37° C. for 2 hours. The EcoRI-digested DNA was extracted once with phenol, extracted twice with chloroform, precipitated with ethanol, and resuspended in 3 μl of 10X ligase buffer and 20 μl of H₂O. The fragment, which is about 770 bp in size and encodes the trpPO and the amino-terminus of TPA, thus prepared had one EcoRI-compatible end and one blunt end and was ligated into EcoRI-SmaI-digested plasmid pUC19 to form plasmid pUC19TPAFE.

About 2 μl of plasmid pUC19 (available from Bethesda Research Laboratories) were dissolved in 2 μl of 10X SmaI buffer (0.2M KCl; 60 mM Tris-HCl, pH=8.0; 60 mM MgCl₂; 60 mM 2-mercaptoethanol; and 1 mg/ml BSA) and 16 μl of H₂O. About 2 μl (~10 units) of restriction enzyme SmaI were added to the solution of DNA, and the resulting reaction was incubated at 25° C. for 2 hours. The SmaI-digested plasmid pUC19 DNA was precipitated with ethanol, collected by centrifugation, and resuspended in 2 μl of 10X EcoRI buffer and 16 μl of H₂O. About 2 μl (~10 units) of restriction enzyme EcoRI were added to the solution of SmaI-digested plasmid pUC19 DNA, and the resulting reaction was incubated at 37° C. for 2 hours. The EcoRI-SmaI-digested plasmid pUC19 DNA was extracted once with phenol, extracted twice with chloroform, and resuspended in 5 μl of TE buffer.

The EcoRI-SmaI-digested plasmid pUC19 DNA was added to the solution containing the ~770 bp EcoRI-blunt end restriction fragment derived from plasmid pTPA103derNdeI. About 2 μl (~1000 units) of T4 DNA ligase were added to the mixture of DNA, and the resulting reaction was incubated at 16° C. overnight. The ligated DNA constituted the desired plasmid pUC19TPAFE.

The multiple-cloning site of plasmid pUC19, which comprises the EcoRI and SmaI recognition sequences utilized in the construction of plasmid pUC19TPAFE, is located within the coding sequence for the lacZ α fragment. Expression of the lacZ α fragment in cells that contain the lacZ ΔM15 mutation, a mutation in the lacZ gene that encodes β-galactosidase, allows those cells to express a functional β-galactosidase molecule and thus allows those cells to hydrolyze X-Gal (5-bromo-4-chloro-3-indolyl-β-D-galactopyranoside), a colorless compound, to its indigo-colored hydrolysis product. Insertion of DNA into the multiple-cloning site of plasmid pUC19 interrupts the coding sequence for the lacZ α fragment, and cells with the lacZ ΔM15 mutation that host such a plasmid are unable to hydrolyze X-Gal (this same principle is utilized when cloning into plasmid pUC8; see Example 2). The ligated DNA that constituted plasmid pUC19TPAFE was used to transform E. coli K12 RR1ΔM15 (NRRL B-15440) cells made competent for transformation in substantial accordance with the procedure of Example 2.

The transformed cells were plated on L agar containing 100 μg/ml ampicillin; 40 μg/ml X-Gal; and 1 mM IPTG. Colonies that failed to exhibit the indigo color were subcultured and used to prepare plasmid DNA; the E. coli K12 RR1ΔM15/pUC19TPAFE transformants were identified by restriction enzyme analysis of their plasmid DNA. Plasmid pUC19TPAFE DNA was isolated from the E. coli K12 RR1ΔM15/pUC19TPAFE cells for use in subsequent constructions in substantial accordance with the procedure of Example 3.

About 7 μg of plasmid pUC19TPAFE in 20 μl of TE buffer were added to 10 μl of 10X HpaI buffer (0.2M KCl; 0.1M Tris-HCl, pH=7.4; and 0.1M MgCl$_2$) and 70 μl of H$_2$O. About 3 μl (~6 units) of restriction enzyme HpaI were added to the solution of plasmid pUC19TPAFE DNA, and the resulting reaction was incubated at 37° C. for 20 minutes; the short reaction period was designed to yield a partial HpaI digest. The reaction was adjusted to 150 μl of 1X BamHI buffer (150 mM NaCl; 10 mM Tris-HCl, pH=8.0; and 10 mM MgCl$_2$; raising the salt concentration inactivates HpaI). About 1 μl (~16 units) of restriction enzyme BamHI were added to the solution of partially-HpaI-digested DNA, and the resulting reaction was incubated at 37° C. for 90 minutes.

The BamHI-partially-HpaI-digested plasmid pUC19TPAFE DNA was concentrated by ethanol precipitation, loaded onto a 1.5% agarose gel, and the ~3.42 kb HpaI-BamHI restriction fragment that comprises the replicon, β-lactamase gene, and all of the TPA-encoding DNA of plasmid pUCATPAFE was isolated from the gel by cutting out the segment of the gel that contained the desired fragment, freezing the segment, and then squeezing the liquid from the segment. The DNA was precipitated from the liquid by an ethanol precipitation. About 1 μg of the desired fragment was obtained and suspended in 20 μl of TE buffer.

About 10 μg of plasmid pTPA103 in 10 μl of TE buffer were dissolved in 10 μl of 10X ScaI buffer (1.0M NaCl; 60 mM Tris-HCl, pH=7.4; and 60 mM MgCl$_2$) 10 mM DTT; and 1 mg/ml BSA) and 80 μl of H$_2$O. About 3 μl (~18 units) of restriction enzyme ScaI were added to the solution of plasmid pTPA103 DNA, and the resulting reaction was incubated at 37° C. for 90 minutes. The reaction volume was adjusted to 150 μl of 1X BamHI buffer, and about 1 μl (~16 units) of restriction enzyme BamHI was added to the mixture, which was then incubated at 37° C. for 90 minutes. The DNA was precipitated with ethanol, collected by centrifugation, and resuspended in preparation for electrophoresis. The ScaI-BamHI-digested plasmid pTPA103 DNA was loaded onto a 1.5% agarose gel and electrophoresed until the ~1.015 kb ScaI-BamHI restriction fragment was separated from the other digestion products. The ~1.015 ScaI-BamHI restriction fragment that comprises the TPA carboxy-terminus-encoding DNA of plasmid pTPA103 was isolated from the gel; about 0.5 μg of the desired fragment were obtained and dissolved in 20 μl of glass-distilled H$_2$O.

About 2 μl of the ~3.42 kb BamHI-HpaI restriction fragment of plasmid pUC19TPAFE were added to 2 μl of the ~1.015 kb ScaI-BamHI restriction fragment of plasmid pTPA103 together with 2 μl of 10X ligase buffer and 1 μl (~1 Weiss unit; the ligase was obtained from Promega Biotec, 2800 S. Fish Hatchery Road, Madison, Wis. 53711) of T4 DNA ligase, and the resulting reaction was incubated at 16° C. overnight. The ligated DNA constituted the desired plasmid pBW25.

The ligated DNA was used to transform E. coli K12 JM105 (available from BRL) that were made competent for transformation in substantial accordance with the procedure of Example 2, except that 50 mM CaCl$_2$ was used in the procedure. The transformed cells were plated on BHI (Difco Laboratories, Detroit, Mich.) containing 100 μg/ml ampicillin, and the E. coli K12 JM105/pBW25 transformants were identified by restriction enzyme analysis of their plasmid DNA. Digestion of plasmid pBW25 with restriction enzyme EcoRI yields ~3.38 kb and ~1.08 kb restriction fragments. Plasmid pBW25 is prepared for use in subsequent constructions in substantial accordance with the procedure of Example 3.

C. Site-Specific Mutagenesis of the TPA Coding Region and Construction of Plasmid pBW28

About 5 μg of plasmid pBW25 in 10 μl of glass-distilled H$_2$O were added to about 10 μl of 10X HindIII reaction buffer and 80 μl of H$_2$O. About 1 μl (~20 units) of restriction enzyme HindIII was added to the solution of plasmid pBW25 DNA, and the resulting reaction was incubated at 37° C. for 90 minutes. About 3 μl (~24 units) of restriction enzyme EcoRI and 10 μl of 1M Tris.HCl, pH=7.6, were added to the solution of HindIII-digested plasmid pBW25 DNA, and the resulting reaction was incubated at 37° C. for 90 minutes. The EcoRI-HindIII-digested plasmid pBW25 DNA was concentrated by ethanol precipitation, loaded onto a 1.5% agarose gel, and electrophoresed until the ~810 bp EcoRI-HindIII restriction fragment was separated from the other digestion products. About 0.5 μg of the ~810 bp EcoRI-HindIII restriction fragment was isolated from the gel, prepared for ligation, and resuspended in 20 μl of glass-distilled H$_2$O.

About 4.5 μg of the replicative form (RF) of M13mp8 DNA (available from New England Biolabs) in 35 μl of glass-distilled H$_2$O were added to 10 μl of 10X HindIII buffer and 55 μl of H$_2$O. About 1 μl (~20 units) of restriction enzyme HindIII was added to the solution of M13mp8DNA, and the resulting reaction was incubated at 37° C. for 1 hour. About 3 μl (~24 units) of restriction enzyme EcoRI and about 10 μl of 1M Tris.HCl, pH=7.6, were added to the solution of HindIII-digested M13mp8 DNA, and the resulting reaction was incubated at 37° C. for 1 hour. The HindIII-EcoRI-digested M13mp8 DNA was collected by ethanol precipitation, resuspended in preparation for agarose gel electrophoresis, and the large restriction fragment isolated by gel electrophoresis. About 1 μg of the large EcoRI-HindIII restriction fragment of M13mp8 was obtained and suspended in 20 μl of glass-distilled H$_2$O. About 2 μl of the large EcoRI-HindIII restriction fragment of M13mp8, 2 μl of 10X ligase buffer, 12 μl of H$_2$O and ~1 (~1 Weiss unit) of T4 DNA ligase were added to 3 μl of the ~810 bp EcoRI-HindIII restriction fragment of plasmid pBW25, and the resulting ligation reaction was incubated at 16° C. overnight.

E. coli JM103 cells, available from BRL, were made competent and transfected with the ligation mix in substantial accordance with the procedure described in the BRL M13 Cloning/'Dideoxy' Sequencing Instruction Manual, except that the amount of DNA used per transfection was varied. Recombinant plaques were identified by insertional inactivation of the β-galactosidase α-fragment-encoding gene, which results in the loss of the ability to cleave X-gal to its indigo-colored cleavage product. For screening purposes, six white plaques were picked into 2.5 ml of L broth, to which was added 0.4 ml of E. coli K12 JM103, cultured in minimal media stock to insure retention of the F episome that carries proAB, in logarithmic growth phase. The plaque-containing solutions were incubated in an air-shaker at 37° C. for 8 hours. Cells from 1.5 ml aliquots were pelleted and RF DNA isolated in substantial accordance with the alkaline miniscreen procedure of Birnboim and Doly, 1979, Nuc. Acids Res. 7:1513. The remainder of each culture was stored at 4° C. for stock. The desired phage, designated pM8BW26, contained the ~810 bp EcoRI-HindIII restriction fragment of plasmid pBW25 ligated to the ~7.2 kb EcoRI-HindIII restriction fragment of M13mp8.

About fifty ml of log phase *E. coli* JM103 were infected with pM8BW26 and incubated in an air-shaker at 37° C. for 18 hours. The infected cells were pelleted by low speed centrifugation, and single-stranded pM8BW26 DNA was prepared from the culture supernatant by scaling up the procedure given in the Instruction manual. Single-stranded pM8BW26 was mutagenized in substantial accordance with the teaching of Adelman et al., 1983, DNA 2(3): 183–193, except that the Klenow reaction was done at room temperature for 30 minutes, then at 37° C. for 60 minutes, then at 10° C. for 18 hours. In addition, the S1 treatment was done at 20° C., the salt concentration of the buffer was one-half that recommended by the manufacturer, and the M13 sequencing primer (BRL) was used. The synthetic oligodeoxyribonucleotide primer used to delete the coding sequence for amino acid residues 87 through 261 of native TPA was

5'-GGGAAGTGCTGTGAAATATCCACCTGCGGCCT GAGA-3'.

The resulting mutagenesis mix was used to transfect *E. coli* K12 JM103 in substantial accordance with the infection procedure described above. Desired mutants were identified by restriction enzyme analysis of RF DNA and by Maxam and Gilbert DNA sequencing. The desired mutant, which had the coding sequence for amino acid residues 87 through 261 of native TPA deleted, was designated pM8BW27.

To construct plasmid pBW28, a variety of DNA fragments are needed. The first of these fragments was obtained by adding ~20 μg of RF pM8BW27 DNA in 20 μl of glass-distilled H₂O to 10 μl of 10X NdeI buffer and 60 μl of H₂O. About 10 μl (~50 units) of restriction enzyme NdeI were added to the mixture of plasmid pM8BW27 DNA, and the resulting reaction was incubated at 37° C. for two hours. The NdeI-digested plasmid pM8BW27 DNA was precipitated with ethanol, collected by centrifugation, and resuspended in 10 μl of 10X EcoRI buffer and 90 μl of H₂O. About 10 μl (~50 units) of restriction enzyme EcoRI were added to the solution of NdeI-digested plasmid pM8BW27 DNA, and the resulting reaction was incubated at 37° C. for 2 hours. The EcoRI-NdeI-digested plasmid pM8BW27 DNA was electrophoresed on an agarose gel until the ~560 bp NdeI-EcoRI restriction fragment, which contains the portion of TPA coding sequence that spans the site of deletion, was separated from the other digestion products. The ~560 bp NdeI-EcoRI restriction fragment was isolated from the gel; about 0.5 μg of the desired fragment was obtained and suspended in 20 μl of glass-distilled H₂O.

The second fragment needed to construct plasmid pBW28 is synthesized one strand at a time on an automated DNA synthesizer. The two complementary strands, which will hybridize to form a double-stranded DNA segment with XbaI and NdeI overlaps, are kinased and annealed in substantial accordance with the procedure of Example 9A. The linker has the following structure:

The third fragment needed to construct plasmid pBW28 was prepared by adding ~20 μg of plasmid pTPA103 in 20 μl of TE buffer to 10 μl of 10X BamHI buffer and 60 μl of H₂O. About 10 μl (~50 units) of restriction enzyme BamHI were added to the solution of plasmid pTPA103 DNA, and the resulting reaction was incubated at 37° C. for 2 hours. The BamHI-digested plasmid pTPA103 DNA was precipitated with ethanol, collected by centrifugation, and resuspended in 10 μl of 10X EcoRI buffer and 80 μl of H₂O. About 10 μl (~50 units) of restriction enzyme EcoRI were added to the solution of BamHI-digested plasmid pTPA103 DNA, and the resulting reaction was incubated at 37° C. for 2 hours. The BamHI-EcoRI-digested plasmid pTPA103 DNA was loaded onto an agarose gel and electrophoresed until the ~689 bp EcoRI-BamHI restriction fragment, which comprises the coding sequence for the carboxy-terminus of TPA, was separated from the other digestion products. About 0.5 μg of the ~689 bp fragment was isolated from the gel and then resuspended in 10 μl of glass-distilled H₂O.

The final fragment necessary to construct plasmid pBW28 was isolated from plasmid pL110, which is a plasmid disclosed and claimed in U.S. patent application Ser. No. 769,221, filed Aug. 26, 1985, abandoned. The construction of plasmid pL110 is disclosed in Example 9d, the following section of the present Example.

About 25 μg of plasmid pL110 in 25 μl of TE buffer were added to 10 μl of 10X XbaI buffer (0.5M NaCl; 60 mM Tris-HCl, pH=7.9; 60 mM MgCl₂; and 1 mg/ml BSA) and 55 μl of H₂O. About 10 μl (~50 units) of restriction enzyme XbaI were added to the solution of plasmid pL110 DNA, and the resulting reaction was incubated at 37° C. for 2 hours. The XbaI-digested plasmid pL110 DNA was precipitated with ethanol, collected by centrifugation, and resuspended in 10 μl of 10X BamHI buffer and 89 μl of H₂O. About 1 μl (~5 units) of restriction enzyme BamHI was added to the solution of XbaI-digested plasmid pL110 DNA, and the resulting reaction was incubated at 37° C. for 30 minutes to obtain a partial BamHI digest. The XbaI-partially-BamHI-digested plasmid pL110 DNA was loaded onto an agarose gel and electrophoresed until the ~6.0 kb XbaI-BamHI fragment was clearly separated from the other digestion products. The ~6.0 kb restriction fragment was isolated from the gel; about 0.5 μg of the ~6.0 kb XbaI-BamHI restriction fragment was obtained and suspended in about 40 μl of glass-distilled H₂O. This ~6.0 kb XbaI-BamHI restriction fragment comprises all of plasmid pL110 except the EK-BGH-encoding DNA.

To construct plasmid pBW28, the following fragments are mixed together: about 0.1 μg (~8 μl) of the ~6.0 kb BamHI-XbaI restriction fragment of plasmid pL110; about 0.05 μg (42 μl) of the ~560 bp NdeI-EcoRI restriction fragment of plasmid pM8BW27; about 0.1 μg (~2 μl) of the ~689 bp EcoRI-BamHI restriction fragment of plasmid pTPA103; and about 0.02 μg (~1 μl) of the ~45 bp XbaI-NdeI synthetic linker. About 2 μl of 10X ligase buffer and 1 μl (~1 Weiss unit) of T4 DNA ligase are added to the mixture of DNA, and the resulting ligation reaction is incubated at 4° C. overnight for 2 hours. The ligated DNA constituted the desired plasmid pBW28.

```
       XbaI
5'-CTAGAGGGTATTAATAATGTATCGATTTAAATAAGGAGGAATAACA-3'
       ||||||||||||||||||||||||||||||||||||||||||
       TCCCATAATTATTACATAGCTAAATTTATTCCTCCTTATTGTAT
                                                NdeI
```

The ligated DNA was used to transform E. coli K12 MM294 (NRRL B-15625) made competent in substantial accordance with the procedure of Example 2, except that 50 mM CaCl$_2$ was used in the procedure. Due to the presence of the lambda pL promoter and the gene encoding the temperature-sensitive lambda pL repressor on plasmid pBW28, the transformation procedure and culturing of transformants were varied somewhat. The cells were not exposed to temperatures greater than 32° C. during transformation and subsequent culturing. The following section of this Example relates more fully the procedures for handling plasmids that encode the lambda pL promoter and its temperature-sensitive repressor. The desired E. coli K12 MM294/pBW28 transformants were identified by their tetracycline-resistant, ampicillin-sensitive phenotype and by restriction enzyme analysis of their plasmid DNA.

D. Construction of Plasmid pL110

Plasmid pL110 was constructed using plasmid pKC283 as starting material. Lyophils of E. coli K12 BE1201/pKC283 are obtained from the NRRL under the accession number NRRL B-15830. The lyophils are decanted into tubes containing 10 ml of L broth and incubated two hours at 32° C., at which time the cultures are made 50 µg/ml in ampicillin and then incubated at 32° C. overnight. The E. coli K12 BE1201/pKC283 cells were cultured at 32° C., because plasmid pKC283 comprises the pL promoter and because E. coli K12 BE1201 cells comprise a temperature-sensitive cI repressor gene integrated into the cellular DNA. When cells that comprise a wild-type lambda pL repressor gene or when cells that do not comprise a lambda pL promoter are utilized in this plasmid isolation procedure, as described in subsequent Examples herein, the temperature of incubation is 37° C.

A small portion of the overnight culture is placed on L-agar plates containing 50 µg/ml ampicillin in a manner so as to obtain a single colony isolate of E. coli K12 BE1201/pKC283. The single colony obtained was inoculated into 10 ml of L broth containing 50 µg/ml ampicillin and incubated overnight at 32° C. with vigorous shaking. The 10 ml overnight culture was inoculated into 500 ml of L broth and incubated at 32° C. with vigorous shaking until the culture reached stationary phase. Plasmid pKC283 DNA was then prepared from the cells in substantial accordance with the procedure of Example 3. About 1 mg of plasmid pKC283 was obtained and stored at 4° C. in TE buffer at a concentration of about 1 µg/µl.

About 10 µl (~10 µg) of the plasmid pKC283 DNA were mixed with 20 µl 10X medium-salt restriction buffer (500 mM NaCl; 100 mM Tris-HCl, pH=7.5; 100 mM MgCl$_2$; and 10 mM DTT), 20 µl 1 mg/ml BSA, 5 µl restriction enzyme PvuII (~25 units), and 145 µl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 µl of TE buffer.

About 600 picomoles (pM) of XhoI linkers (5'-CCTCGAGG-3') were kinased in a mixture containing 10 µl of 5X Kinase Buffer (300 mM Tris-HCl, pH=7.8; 50 mM MgCl$_2$; and 25 mM DTT), 5 µl of 5 mM ATP, 24 µl of H$_2$O, 0.5 µl of T4 polynucleotide kinase (about 2.5 units as defined by P-L Biochemicals), 5 µl of 1 mg/ml BSA, and 5 µl of 10 mM spermidine by incubating the mixture at 37° C. for 30 minutes. About 12.5 µl of the kinased XhoI linkers were added to the 5 µl of PvuII-digested plasmid pKC283 DNA, and then, 2.5 µl of 10X ligase buffer, 2.5 µl (about 2.5 units as defined by P-L Biochemicals) of T4 DNA ligase, 2.5 µl of 10 mM spermidine, and 12.5 µl of water were added to the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10.0 mM MgCl$_2$; and 1 mM DTT). About 10 µl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX.

E. coli K12 MO($\lambda^+$), available from the NRRL under the accession number NRRL B-15993, comprises the wild-type lambda pL cI repressor gene, so that transcription from the lambda pL promoter does not occur in E. coli K12 MO($\lambda^+$) cells. Single colonies of E. coli K12 MO($\lambda^+$) are isolated, and a 10 ml overnight culture of the cells is prepared; no ampicillin is used in the growth media. Fifty µl of the overnight culture were used to inoculate 5 ml of L broth, which also contained 10 mM MgSO$_4$ and 10 mM MgCl$_2$. The culture was incubated at 37° C. overnight with vigorous shaking. The following morning, the culture was diluted to 200 ml with L broth containing 10 mM MgSO$_4$ and 10 mM MgCl$_2$. The diluted culture was incubated at 37° C. with vigorous shaking until the O.D.$_{590}$ was about 0.5, which indicated a cell density of about $1 \times 10^8$ cells/ml. The culture was cooled for ten minutes in an ice-water bath, and the cells were then collected by centrifugation at 4000 Xg for 10 minutes at 4° C. The cell pellet was resuspended in 100 ml of cold 10 mM NaCl and then immediately re-pelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared above; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred µl aliquots were plated on L-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 3, but the CsCl gradient step was omitted until the desired E. coli K12 MO($\lambda^+$)/pKC283PX transformants were identified.

Ten µg of plasmid pKC283PX DNA were dissolved in 20 µl of 10X high-salt buffer, 20 µl 1 mg/ml BSA, 5 µl (~50 units) of restriction enzyme BglII, 5 µl (~50 units) of restriction enzyme XhoI, and 150 µl of water, and the resulting reaction was incubated at 37° C. for two hours. The reaction was stopped; the BglII-XhoI digested DNA was precipitated, and the DNA was resuspended in 5 µl of TE buffer.

A DNA linker with single-stranded DNA ends characteristic of BglII and XhoI restriction enzyme cleavage was synthesized using an automated DNA synthesizer and kinased as described in Example 9A. The DNA linker had the following structure:

```
5'GATCTATTAACTCAATCTAGAC-3'
  ||||||||||||||||||||
3'-ATAATTGAGTTAGATCTGAGCT-5'
```

The linker and BglII-XhoI-digested plasmid pKC283PX were ligated in substantial accordance with the ligation procedure described above. The ligated DNA constituted the desired plasmid pKC283-L. The plasmid pKC283-L DNA was used to transform *E. coli* K12 MO($\lambda^+$), and the resulting *E. coli* K12 MO($\lambda^+$)/pKC283-L transformants were identified by their ampicillin-resistant phenotype and by restriction enzyme analysis of their plasmid DNA.

About 10 μg of plasmid pKC283-L DNA were dissolved in 20 μl 10X high-salt buffer, 20 μl 1 mg/ml BSA, 5 μl (~50 units) restriction enzyme XhoI, and 155 μl of H$_2$O, and the resulting reaction was incubated at 37° C. for two hours. The XhoI-digested plasmid pKC283-L DNA was then precipitated and resuspended in 2 μl 10X nick-translation buffer (0.5M Tris-HCl, pH=7.2; 0.1M MgSO$_4$; and 1 mM DTT), 1 μl of a solution 2 mM in each of the deoxynucleotide triphosphates, 15 μl of H$_2$O, 1 μl (~6 units as defined by P-L Biochemicals) of Klenow, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the linker ligation procedures described above. After the ligation reaction, the DNA was digested with about 100 units of BamHI for about 2 hours at 37° C. in high-salt buffer. After the BamHI digestion, the DNA was prepared for ligation, and the ~5.9 kb BamHI restriction fragment was circularized by ligation and transformed into *E. coli* K12 MO($\lambda^+$) in substantial accordance with the procedures described above. The *E. coli* K12 MO($\lambda^+$)/pKC283-LB transformants were identified, and then, plasmid pKC283-LB DNA was prepared from the transformants in substantial accordance with the procedure of Example 3.

About 10 μg of plasmid pKC283PX were digested with restriction enzyme SalI in high-salt buffer, treated with Klenow, and ligated to EcoRI linkers (5'-GAGGAATTCCTC-3') in substantial accordance with the procedures described above. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform *E. coli* K12 MO($\lambda^+$), and after the *E. coli* K12 MO($\lambda^+$)/pKC283PRS transformants were identified, plasmid pKC283PRS DNA was prepared from the transformants in substantial accordance with the procedure of Example 3.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2–3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 ug of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB. The ligated DNA constituted the desired plasmid pL32. Plasmid pL32 was transformed into *E. coli* K12 MO($\lambda^+$) cells; plasmid pL32 DNA was prepared from the *E. coli* K12 MO($\lambda^+$)/pL32 transformants in substantial accordance with the procedure of Example 3. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together.

Plasmid pCC101 is disclosed in Example 3 of U.S. patent application Ser. No. 586,581, filed 6 Mar. 1984, U.S. Pat. No. 4,745,069, incorporated herein by reference. To isolate the EK-BGH-encoding DNA, about 10 μg of plasmid pCC101 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated from the gel and prepared for ligation.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid pCC101 to yield plasmid pL47. Plasmid pL47 was transformed into *E. coli* K12 MO($\lambda^+$), and the *E. coli* K12 MO($\lambda^+$)/pL47 transformants were identified. Plasmid pL47 DNA was prepared from the transformants in substantial accordance with the procedures of Example 3.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued 13 Mar. 1984.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and then treated with Klenow in substantial accordance with the procedure described above. After the Klenow reaction, the EcoRI-digested, Klenow-treated plasmid pPR12 DNA was recircularized by ligation, and the ligated DNA, which constituted the desired plasmid pPR12ΔR1, was used to transform *E. coli* K12 RV308 (NRRL B-15624); transformants were selected based on tetracycline (10 ug/ml) resistance. After the *E. coli* K12 RV308/pPR12ΔR1 transformants were identified, plasmid pPR12ΔR1 DNA was prepared from the transformants in substantial accordance with the procedure of Example 3.

About 10 μg of plasmid pPR12ΔR1 were digested with about 50 units of restriction enzyme EcoI in 200 μl of medium-salt buffer at 37° C. for 2 hours. The AvaI-digested plasmid pPR12ΔR1 DNA was precipitated and then treated with Klenow. After the Klenow reaction, the AvaI-digested, Klenow-treated plasmid pPR12ΔR1 DNA was ligated to EcoR1 linkers (5'-GAGGAATTCCTC-3'), precipitated, resuspended in about 200 μl of high-salt buffer containing about 50 units of restriction enzyme EcoRI, and incubated at 37° C. for about 2 hours. After the EcoRI digestion, the reaction mixture was loaded onto a low-melting agarose gel, and the ~5.1 kb EcoRI restriction fragment was purified from the gel and recircularized by ligation to yield the desired plasmid pPR12AR1. The plasmid pPR12AR1 DNA was transformed into *E. coli* K12 RV308; selection of transformants was based on tetracycline resistance. Plasmid pPR12AR1 DNA was prepared from the transformants in substantial accordance with the procedure of Example 3.

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoRI restriction fragment of plasmid pPR12AR1 was isolated and prepared for ligation.

About 10 ug of plasmid pL47 were digested with restriction enzymes PstI and BamHI in 200 ul of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation. In a separate reaction, about 10 ug of plasmid pL47 DNA were digested with restriction enzymes EcoRI and BamHI in 200 ul of high-salt buffer at 37° C. for two hours, and the ~1.03 kb EcoRI-BamHI restriction fragment that comprised the lambda pL transcription activating sequence, the *E. coli lpp* translation activating sequence, and the EK-BGH-encoding DNA was isolated and prepared for ligation.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308. Tetracycline resistance was used as the basis for selecting transformants.

Two PstI restriction enzyme recognition sites are present in the EK-BGH coding region that are not depicted in the restriction site and function maps presented in the accompanying drawings.

E. Final Construction of Plasmid pBW32

Approximately 10 μg of plasmid pSV2-β-globin DNA (NRRL B-15928) were dissolved in 10 μl 10X HindIII reaction buffer, 5 μl (~50 units) restriction enzyme HindIII, and 85 μl H₂O, and the reaction was placed at 37° C. for 2 hours. The reaction mixture was then made 0.15M in LiCl, and after the addition of 2.5 volumes of ethanol and incubation in a dry ice-ethanol bath, the DNA was pelleted by centrifugation.

The DNA pellet was dissolved in 10 μl 10X BglII buffer, 5 μl (~50 units) restriction enzyme BglII, and 85 μl H₂O, and the reaction was placed at 37° C. for two hours. After the BglII digestion, the reaction mixture was loaded onto a 0.85% agarose gel, and the fragments were separated by electrophoresis. The gel was visualized using ethidium bromide and ultraviolet light, and the band containing the desired ~4.2 kb HindIII-BglII fragment was excised from the gel as previously described. The pellet was resuspended in 10 μl of H₂O and constituted ~5 μg of the desired ~4.2 kb HindIII-BglII restriction fragment of plasmid pSV2-β-globin. The ~2.0 kb HindIII-BamHI restriction fragment of plasmid pTPA103 that encodes TPA was isolated from plasmid pTPA103 in substantial accordance with the foregoing teaching. About 5 μg of the ~2.0 kb HindIII-BamHI restriction fragment of plasmid pTPA103 were obtained, suspended in 10 μl of H₂O, and stored at -20° C.

Two μl of the ~4.2 kb BglII-HindIII restriction fragment of plasmid pSV2-β-globin and 4 μl of the ~2.0 kb HindIII-BamHI fragment of plasmid pTPA103 were mixed together and then incubated with 2 μl of 10X ligase buffer, 11 μl of H₂O, and 1 μl of T4 DNA ligase (~500 units) at 4° C. overnight. The ligated DNA was used to transform *E. coli* K12 RR1 cells (NRRL B-15210) made competent for transformation in substantial accordance with the teaching of Example 2. Plasmid DNA was obtained from the *E. coli* K12 RR1/pTPA301 transformants in substantial accordance with the procedure of Example 3.

Plasmid pSV2-dhfr comprises a dihydrofalate reductase (dhfr) gene useful for selection of transformed eukaryotic cells and amplification of DNA covalently linked to the dhfr gene. Ten μg of plasmid pSV2-dhfr (isolated from *E. coli* K12 HB101/pSV2-dhfr, ATCC 37146) were mixed with 10 μl 10X PvuII buffer, 2 μl (~20 units) PvuII restriction enzyme, and 88 μl of H₂O, and the resulting reaction was incubated at 37° C. for two hours. The reaction was terminated by phenol and chloroform extractions, and then, the PvuII-digested plasmid pSV2-dhfr DNA was precipitated and collected by centrifugation.

BamHI linkers (5'-CGGATCCCG-3') were kinased and prepared for ligation by the following procedure. To 1 μg of linker in 5 μl H₂O was added: 10 μl 5X Kinase salts (300 mM Tris-HCl, pH=7.8; 50 mM MgCl₂; and 25 mM DTT), 5 μl of 5 mM ATP, 5 μl of BSA (1 mg/ml), 5 μl of 10 mM spermidine, 19 μl of H₂O, and 1 μl of poly-nucleotide Kinase (10 units/μl). This reaction was then incubated at 37° for 60 minutes and stored at -20° C. Five μl (~5 μg) of the PvuII-digested plasmid pSV2-dhfr and 12 μl (~0.25 μg) of the kinased BamHI linkers were mixed and incubated with 11 μl of H₂O, 2 μl 10X ligase buffer, and 1 μl (~1000 units) of T4 DNA ligase at 16° C. overnight.

Ten μl of 10X BamHI reaction buffer, 10 μl (~50 units) of BamHI restriction enzyme, and 48 μl of H₂O were added to the ligation reaction mixture, which was then incubated at 37° C. for 3 hours. The reaction was loaded onto a 1% agarose gel, and the desired ~1.9 kb fragment, which comprises the dhfr gene, was isolated from the gel. All linker additions performed in these examples were routinely purified on an agarose gel to reduce the likelihood of multiple linker sequences in the final vector. The ~3 μg of fragment obtained were suspended in 10 μl of TE buffer.

Next, approximately 15 μl (~1 μg) of plasmid pTPA301 were digested with BamHI restricton enzyme as taught above. Because there is a unique BamHI site in plasmid pTPA301, this BamHI digestion generates linear plasmid pTPA301 DNA. The BamHI-digested plasmid pTPA301 was precipitated with ethanol and resuspended in 94 μl of H₂O and phosphatased using 1 μl of Calf-Intestinal Alkaline phosphatase (Collaborative Research, Inc., 128 Spring Street, Lexington, Mass. 02173), and 5 μl of 1M Tris-HCl, pH=9.0, at 65° C. for 45 min. The DNA was extracted with phenol:chloroform, then extracted with chloroform:isoamyl alcohol, ethanol precipitated, and resuspended in 20 μl H₂O. Ten μl (~0.25 μg) of phosphatased plasmid pTPA301 were added to 5 μl of the BamHI, dhfr-gene-containing restriction fragment (~1.5 μg), 3 μl of 10X ligase buffer, 3 μl (~1500 units) of T4 DNA ligase, and 9 μl H₂O. This ligation reaction was incubated at 15° C. overnight; the ligated DNA constituted the desired plasmid pTPA303 DNA.

Plasmid pTPA303 was used to transform *E. coli* K12 RR1 (NRRL B-15210), and the resulting *E. coli* K12 RR1/pTPA303 transformants were identified by their ampicillin-resistant phenotype and by restriction enzyme analysis of their plasmid DNA. Plasmid pTPA303 was isolated from the transformants in substantial accordance with the procedure of Example 3.

To isolate the ~2.7 kb EcoRI-BglII restriction fragment that encodes the pBR322 replicon and β-lactamase gene from plasmid pTPA301, about 10 µg of plasmid pTPA301 are digested to completion in 400 µl total reaction volume with 20 units BglII restriction enzyme in 1X BglII buffer at 37° C. After the BglII digestion, the Tris-HCl concentration is adjusted to 110 mM, and 20 units of EcoRI restriction enzyme are added to the BglII-digested DNA. The EcoRI-BglII-digested DNA is loaded onto an agarose gel and electrophoresed until the ~2.7 kb EcoRI-BglII restriction fragment is separated from the other digestion products, and then, the ~2.7 kb fragment is isolated and prepared for ligation.

To isolate a restriction fragment that comprises the dhfr gene, plasmid pTPA303 was double-digested with HindIII and EcoRI restriction enzymes, and the ~2340 bp EcoRI-HindIII restriction fragment that comprises the dhfr gene was isolated and recovered.

To isolate the ~2 kb HindIII-SstI restriction fragment of plasmid pTPA303 that comprises the coding region for the carboxy-terminus of TPA and the SV40 promoter, plasmid pTPA303 was double digested with HindIII and SstI restriction enzymes in 1X HindIII buffer. The ~1.7 kb fragment was isolated from the gel and prepared for ligation.

To isolate the ~680 bp XhoII (compatible for ligation with the BglII overlap)-SstI restriction fragment of plasmid pBW28 that comprises the coding region for the amino terminus of modified TPA, about 10 µg of plasmid pBW28 were digested with XhoII enzyme to completion in 1X XhoII buffer (0.1M Tris-HCl, pH=8.0; 0.1M $MgCl_2$; 0.1% Triton X-100; and 1 mg/ml BSA). The XhoII-digested DNA was recovered by ethanol precipitation and subsequently digested to completion with SstI enzyme. The XhoII-SstI-digested DNA was loaded onto an acrylamide gel, and the desired fragment was isolated from the gel and prepared for ligation.

Figure 14:
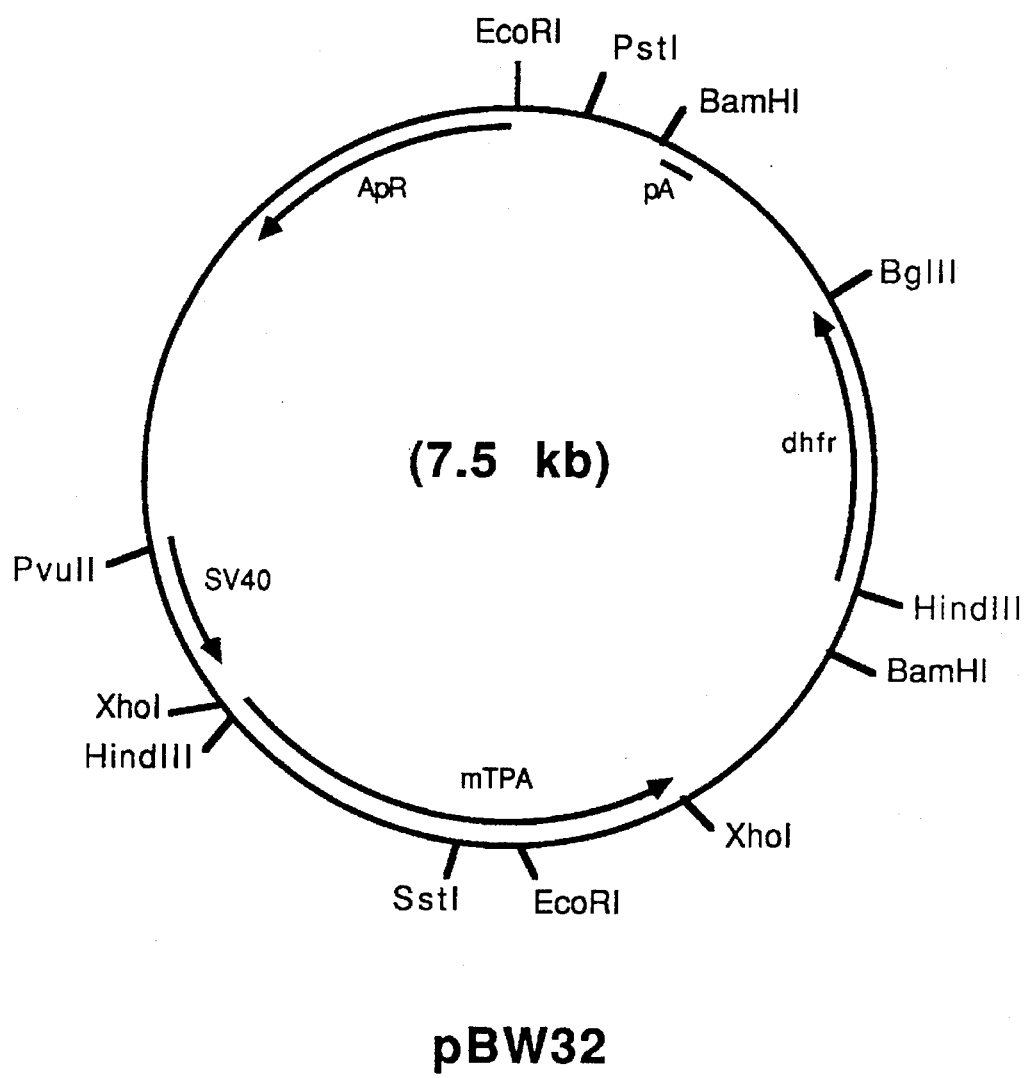
FIG. 14 is a restriction site and function map of plasmid pBW32.

About 0.1 µg of each of the above fragments: the ~2.7 kb EcoRI-BglII restriction fragment of plasmid pTPA301; the ~2.34 kb EcoRI-HindIII restriction fragment of plasmid pTPA303; the ~1.7 kb SstI-HindIII restriction fragment of plasmid pTPA303; and the ~0.68 kb SstI-XhoII restriction fragment of plasmid pBW28 were ligated together to form plasmid pBW32. The ligation mix was used to transform *E. coli* K12 MM294 as taught in Example 2, except that 50 mM $CaCl_2$ was used in the procedure. Transformants were identified by their ampicillin-resistant phenotype and by restriction analysis of their plasmid DNA. Plasmid pBW32 DNA was obtained from the *E. coli* K12 MM294/pBW32 transformants in substantial accordance with the procedure of Example 3. A restriction site and function map of plasmid pBW32 is presented in FIG. 14 of the accompanying drawings.

EXAMPLE 10

Construction of Plasmids pLPChd1, pLPChd2, pLPCdhfr1, and pLPCdhfr2

A. Construction of Plasmids pLPChd1 and pLPChd2

About 20 µg of plasmid pBW32 in 20 µl of TE buffer were added to 10 µl of 10X BamHI buffer and 60 µl of $H_2O$. About 10 µl (~50 units) of restriction enzyme BamHI were added to the solution of plasmid pBW32 DNA, and the resulting reaction was incubated at 37° C. for two hours. The BamHI-digested plasmid pBW32 DNA was precipitated with ethanol, collected by centrifugation, and resuspended in 5 µl of 10X Klenow buffer, 45 µl of $H_2O$ and 2 µl (~100 units) of Klenow enzyme. The reaction was incubated at 16° C. for 30 minutes; then, the reaction mixture was loaded onto an agarose gel and electrophoresed until the digestion products were clearly separated. The ~1.9 kb Klenow-treated, BamHI restriction fragment of plasmid pBW32 that comprises the dhfr gene was isolated from the gel and prepared for ligation in substantial accordance with the procedure of Example 4A. About 4 µg of the desired fragment were obtained and suspended in 5 µl of TE buffer.

About 200 µg of plasmid pLPChyg1 in 100 µl of TE buffer were added to 15 µl of 10X EcoRI buffer and 30 µl of $H_2O$. About 5 µl (~50 units) of restriction enzyme EcoRI were added to the solution of plasmid pLPChyg1 DNA, and the resulting reaction was incubated at 37° C. for about 10 minutes. The short reaction time was calculated to produce a partial EcoRI digestion. Plasmid pLPChyg1 has two EcoRI restriction sites, one of which is within the coding sequence of the hygromycin resistance-conferring (HmR) gene, and it was desired to insert the dhfr-gene-containing restriction fragment into the EcoRI site of plasmid pLPChyg1 that is not in the HmR gene. The partially-EcoRI-digested plasmid pLPChyg1 DNA was loaded onto an agarose gel and electrophoresed until the singly-cut plasmid pLPChyg1 DNA was separated from uncut plasmid DNA and the other digestion products. The singly-cut DNA was isolated from the gel and prepared for ligation in substantial accordance with the procedure of Example 4A. About 2 µg of the singly-EcoRI-cut plasmid pLPChyg1 were obtained and suspended in 25 µl of TE buffer. To this sample, about 5 µl (~25 units) of Klenow enzyme, 5 µl of 10X Klenow buffer, and 40 µl of $H_2O$ were added, and the resulting reaction was incubated at 16° C. for 60 minutes. The Klenow-treated, partially-EcoRI-digested DNA was then extracted twice with phenol and then once with chloroform, precipitated with ethanol, and resuspended in 25 µl of TE buffer.

About 5 µl of the ~1.9 kb Klenow-treated BamHI restriction fragment of plasmid pBW32 and about 5 µl of the singly-EcoRI-cut plasmid pLPChyg1 DNA were mixed together, and 1 µl of 10X ligase buffer, 5 µl of $H_2O$, 1 µl (~500 units) of T4 DNA ligase, and 1 µl (~2 units) of T4 RNA ligase were added to the mixture of DNA, and the resulting reaction was incubated at 16° C. overnight. The ligated DNA constituted the desired plasmids pLPChd1 and pLPChd2, which differ only with respect to the orientation of the ~1.9 kb fragment that comprises the dhfr gene.

Figure 15:
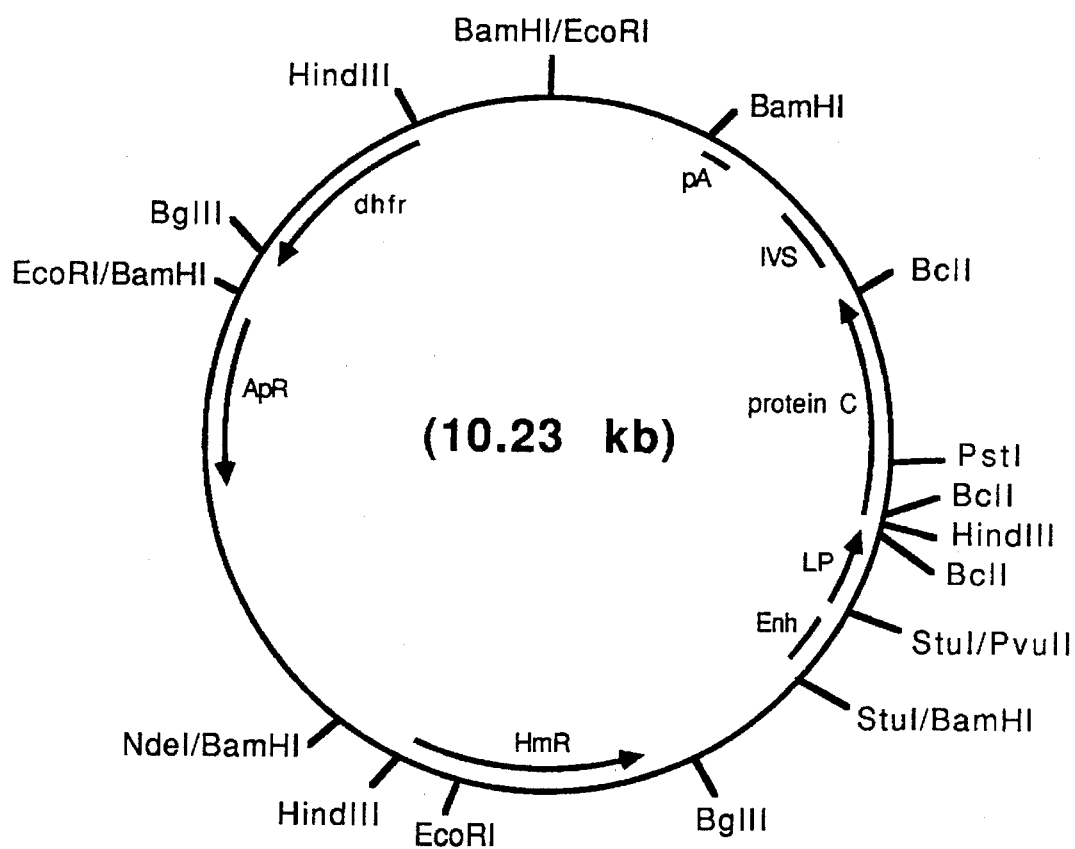
FIG. 15 is a restriction site and function map of plasmid pLPChd1.

The ligated DNA was used to transform *E. coli* K12 HB101 cells made competent for transformation in substantial accordance with the procedure of Example 2. The transformed cells were plated onto L agar containing 100 µg/ml ampicillin, and the ampicillin-resistant transformants were analyzed by restriction enzyme analysis of their plasmid DNA to identify the *E. coli* K12 HB101/pLPChd1 and *E. coli* K12 HB101/pLPChd2 transformants. A restriction site and function map of plasmid pLPChd1 is presented in FIG. 15 of the accompanying drawings. Plasmid pLPChd1 and plasmid pLPChd2 DNA were isolated from the appropriate transformants in substantial accordance with the procedure of Example 3.

Plasmids pLPChd3 and pLPChd4 are similar in structure to plasmids pLPChd1 and pLPChd2. Plasmids pLPChd3 and pLPChd4 are constructed in substantial accordance with the procedure used to construct plasmids pLPChd1 and pLPChd2, except plasmid pLPChyg2 is used as starting material in the procedure rather than plasmid pLPChyg1.

B. Construction of Plasmids pLPCdhfr1 and pLPCdhfr2

About 100 μg of plasmid pBW32 in 100 μl of TE buffer were added to 15 μl of 10X BamHI buffer and 25 μl of H₂O. About 10 μl (~25 units) of restriction enzyme BamHI were added to the solution of plasmid pBW32 DNA, and the resulting reaction was incubated at 37° C. for 2 hours. The BamHI-digested plasmid pBW32 DNA was treated with Klenow in substantial accordance with the procedure in Example 10A. The blunt-ended fragment was precipitated with ethanol, resuspended in 10 μl of TE buffer, loaded onto an agarose gel, and electrophoresed until the ~1.9 kb BamHI restriction fragment that comprises the dihydrofolate reductase gene was separated from the other digestion products. The ~1.9 kb restriction fragment was then isolated from the gel and prepared for ligation in substantial accordance with the procedure of Example 4A; about 10 μg of the desired fragment were obtained and suspended in 50 μl of TE buffer.

About 5 μl of NdeI-StuI-digested plasmid pLPC DNA, as prepared in Example 8, were added to 5 μl of the Klenow-treated, ~1.9 kb BamHI restriction fragment of plasmid pBW32, 1.5 μl of 10X ligase buffer, 1 μl (~1000 units) of T4 DNA ligase, 1 μl (~2 units) of T4 RNA ligase, and 1.5 μl of H₂O. The resulting ligation reaction was incubated at 16° C. overnight; the ligated DNA constituted the desired plasmids pLPCdhfr1 and pLPCdhfr2, which differ only with respect to the orientation of the ~1.9 kb fragment that contains the dhfr gene. The ligated DNA was used to transform *E. coli* K12 HB101 in substantial accordance with the procedure of Example 2. The transformed cells were plated onto L agar containing ampicillin, and the ampicillin-resistant *E. coli* K12 HB101/pLPCdhfr1 and *E. coli* K12 HB101/pLPCdhfr2 transformants were identified by restriction enzyme analysis of their plasmid DNA.

EXAMPLE 11

Construction of Eukaryotic Host Cell Transformants of the Expression Vectors of the Present Invention and Determination of Recombinant Gene Expression Levels in Those Transformants An important aspect of the present invention concerns the use of the BK enhancer and GT enhancer to stimulate gene expression in the presence of the E1A gene product. Because 293 cells constitutively express the E1A gene product, 293 cells are the preferred host for the eukaryotic expression vectors of the present invention. 293 cells are human embryonic kidney cells transformed with adenovirus type 5 (note that any particular type of adenovirus can be used to supply the E1A gene product in the method of the present invention) and are available from the ATCC under the accession number CRL 1573. However, the expression vectors of the present invention function in a wide variety of host cells, even if the E1A gene product is not present. Furthermore, the E1A gene product can be introduced into a non-E1A-producing cell line either by transformation with a vector that comprises the E1A gene (Grinnell et al., 1986, *Mol. Cell. Biol.* 6:3596–3605), such as plasmids pLPCE1A and pLPCE1A1, or with sheered adenovirus DNA, or by infection with adenovirus.

The transformation procedure described below refers to 293 cells as the host cell line; however, the procedure is generally applicable to most eukaryotic cell lines.

293 cells are obtained from the ATCC under the accession number CRL 1573 in a 25 mm² flask containing a confluent monolayer of about 5.5×10⁶ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (Gibco), adding 0.25% trypsin for 1–2 minutes, rinsing with fresh medium, aspirating, and dispensing into new flasks at a subcultivation ratio of 1:5 or 1:10.

One day prior to transformation, cells are seeded at 0.7×10⁶ cells per dish. The medium is changed 4 hours prior to transformation. Sterile, ethanol-precipitated plasmid DNA dissolved in H₂O is used to prepare a 2X DNA-CaCl₂ solution containing 40 μg/ml DNA and 250 mM CaCl₂. 2X HBS is prepared containing 280 mM NaCl, 50 mM Hepes, and 1.5 mM sodium phosphate, with the pH adjusted to 7.05–7.15. The 2X DNA-CaCl₂ solution is added dropwise to an equal volume of sterile 2X HBS. A one ml sterile plastic pipette with a cotton plug is inserted into the mixing tube that contains the 2X HBS, and bubbles are introduced by blowing while the DNA is being added. The calcium-phosphate-DNA precipitate is allowed to form without agitation for 30–45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the medium is replaced with DMEM with 10% fetal bovine serum and the cells allowed to incubate for an additional 72 hours before providing selective pressure. For transformants expressing recombinant human protein C, the growth medium contained 1 to 10 μg/ml vitamin K, a cofactor required for γ-carboxylation of the protein. For plasmids that do not comprise a selectable marker that functions in eukaryotic cells, the transformation procedure utilizes a mixture of plasmids: the expression vector of the present invention that lacks a selectable marker; and an expression vector that comprises a selectable marker that functions in eukaryotic cells. This co-transformation technique allows for the identification of cells that comprise both of the transforming plasmids.

For cells transfected with plasmids containing the hygromycin resistance-conferring gene, hygromycin is added to the growth medium to a final concentration of about 200 to 400 μg/ml. The cells are then incubated at 37° C. for 2–4 weeks with medium changes at 3 to 4 day intervals. The resulting hygromycin-resistant colonies are transferred to individual culture flasks for characterization. The selection of neomycin (G418 is also used in place of neomycin)-resistant colonies is performed in substantial accordance with the selection procedure for hygromycin-resistant cells, except that G418 is added to a final concentration of 300 μg/ml rather than hygromycin. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype.

The use of the dihydrofolate reductase (dhfr) gene as a selectable marker for introducing a gene or plasmid into a dhfr-deficient cell line and the subsequent use of methotrexate to amplify the copy number of the plasmid has been well established in the literature. Although the use of dhfr as a selectable and amplifiable marker in dhfr-producing cells has not been well studied, efficient coamplification in primate cells requires an initial selection using a directly selectable marker before the coamplification using methotrexate. The use of the present invention is not limited by the selectable marker used. Moreover, amplifiable markers such as metallothionein genes, adenosine deaminase genes, or members of the multigene resistance family, exemplified by P-glycoprotein, can be utilized. In 293 cells, it is advantageous to transform with a vector that contains a selectable marker such as the hygromycin B resistance-conferring gene and then amplify using methotrexate, which cannot be used for direct selection of murine dhfr-containing plasmids in 293 cells. The levels of coamplification can be measured using Southern hybridization or other methods known in the art.

Specifically, vectors pLPC and pSV2hyg were transformed into 293 cells, then cultured to the highest level of protein C production (~2 μg/ml in 24 well microtiter plates). The transformants were then subcloned and a clone which was capable of producing about 2 to 3 times as much protein C was selected. This subclone was designated as stable transformant CC311.

EXAMPLE 12

Construction of a High Producing Stable Transformant

*Escherichia coli* K12 AG1/pGTC cells are obtained in lyophil form from the National Regional Research Laboratories in Peoria, Ill. *E. coli* K12 AG1/pGTC was deposited and made part of the permanent stock culture collection of the NRRL on Jan. 18, 1990, and is available to the public under the accession number NRRL B-18593. The culture is reconstituted and the plasmid is purified from the culture in substantial accordance with the teaching of Example 3. Plasmid pGTC comprises the cDNA sequence of human protein C positioned for expression behind the GBMT modified transcription unit of the present invention. A restriction site and function map of plasmid pGTC is presented in FIG. 16 of the accompanying drawings.

Plasmid pGTC was transformed into the CC311 clone in substantial accordance with the teaching of Example 11. In an analogous fashion, plasmids pLPC-hd, pLPC-hyg and pLPC-dhfr were all transformed into 293 cells. Following confirmation of stable transformation and subcloning, the relative levels of human protein C produced by each transformant was tested using the standard ELISA assay described by Grinnell et al., 1987, *Biotechnology* 5:1189–1192, the entire teaching of which is herein incorporated by reference. The results from the assay demonstrated that cells transformed with plasmids pLPC-hd, pLPC-hyg or pLPC-dhfr secreted 120 ng/ml of protein C on the average, while CC311 cells transformed with plasmid pGTC secreted 2930 ng/ml of protein C on the average. Results of these experiments are presented in Table II supra. Protein C can be recovered from the supernatant in accordance with the teaching of Grinnell et al., *Biotechnology*, supra, or Yan, U.S. patent application Ser. No. 07/393,281, filed Aug. 16, 1989, U.S. Pat. No. 4,981,952 the entire teaching of which is herein incorporated by reference.

EXAMPLE 13

Construction of Stable Transformants Secreting Activated Human Protein C

Plasmid pLAPC-IRS comprises the gene sequence of the activated (rather than the zymogen) form of protein C driven by the adenovirus late promoter in conjunction with the BK enhancer and the SV40 T antigen. The construction of plasmid pLAPC-IRS is disclosed in Bang et al., U.S. patent application Ser. No. 07/129,027, filed Dec. 4, 1987, U.S. Pat. No. 4,992,373 the entire teaching of which is herein incorporated by reference. The DNA fragment comprising the gene encoding activated protein C can be easily removed from plasmid pLAPC-IRS by digestion with restriction enzyme BclI.

*Escherichia coli* K12 AG1/pGT-d cells are obtained from the NRRL where they were deposited and made part of the permanent stock culture collection on Jan. 18, 1990. *E. coli* K12 AG1/pGT-d cells are available under the accession number NRRL B-18591. Plasmid pGT-d comprises the GBMT modified transcription unit of present invention along with the murine dhfr gene. Plasmid pGT-d does not contain a gene positioned for expression from the GBMT unit, but rather contains a BclI site positioned for easy insertion of such a gene into the plasmid. A restriction site and function map of plasmid pGT-d is presented in FIG. 17 of the accompanying drawings.

*Escherichia coli* K12 AG1/pGT-h cells are also obtained from the NRRL, where they too were deposited and made part of the permanent stock culture collection on Jan. 18, 1990. *E. coli* K12 AG1/pGT-h cells are available under the accession number NRRL B-18592. Plasmid pGT-d comprises the GBMT unit of the present invention along with the hygromycin resistance conferring gene. Plasmid pGT-h, like plasmid pGT-d, does not contain a gene positioned for expression from the GBMT unit, but rather a BclI site positioned for insertion of any gene. A restriction site and function map of plasmid pGT-h is presented in FIG. 18 of the accompanying drawings.

Plasmid pLAPC-IRS are digested with restriction enzyme BclI and the restriction fragment containing the gene encoding activated protein C is purified. Digestion of plasmid DNA with BclI is inhibited by methylation at adenine in the sequence 5'-GATC-3'. Therefore, plasmid pGT-h was prepared from *E. coli* host cells that lack an adenine methylase, such as that encoded by the dam gene, the product of which methylates the adenine residue in the sequence 5'-GATC-3'. *E. coli* K12 GM48 (NRRL B-15725) lacks a functional dam methylase and so is a suitable host to use for the purpose of preparing plasmid pGT-h DNA for use as starting material in the construction of plasmid pGTAC-h.

*E. coli* K12 GM48 cells were cultured and made competent for transformation, and plasmid pGT-h was used to transform the *E. coli* K12 GM48 cells in substantial accordance with the procedure of Example 2. The transformed cells were plated on L-agar containing ampicillin, and once the ampicillin-resistant, *E. coli* K12 GM48/pGT-h transformants had formed colonies, one such colony was used to prepare plasmid pGT-h DNA in substantial accordance with the procedure of Example 2. About 1 mg of plasmid pGT-h DNA was obtained and suspended in about 1 ml of TE buffer. Plasmid pGT-h is then digested with restriction enzyme BclI, the vector is purified and ligated to the fragment containing the activated protein C gene, in substantial accordance with the earlier Examples. This reaction forms plasmid pGTAC-h, which comprises the gene encoding activated protein C positioned for expression by the GBMT modified transcription unit.

Plasmids pLAPC-IRS and pGTAC-h were then transformed into 293 cells in substantial accordance with the teaching of Example 11. After growth of individual clones to confluence in a 0.9 cm² surface area, the average expression levels of the cells were compared using the standard protein C ELISA assay. The pLAPC-IRS culture produced approximately 33 ng/ml of activated protein C on the average, while the pGTAC-h culture produced approximately 1460 ng/ml of activated protein C on the average. The results of these experiments are shown in Table II.

EXAMPLE 14

Transient Expression

Relative promoter strength can be determined also by using transient expression assay systems, often based upon the expression of chloramphenicol acetyl transferase (CAT). One such method for CAT assays is disclosed by Grinnell et al., 1986, *Mol. Cell. Biol.* 6:3596–3605. An expression vector for the expression of CAT is constructed by first mixing 5 μl of plasmid pGTC (1 μg/ml) grown in GM48 in substantial accordance to the procedure in Example 13, 5 μl of 10X BclI buffer (1.5M KCl, 100 mM Tris-HCl, pH 7.4 and 100 mM MgCl$_2$), 5 μl restriction enzyme BclI and 35 μl of water. After one hour at 37° C., the 5303 base pair vector fragment is isolated on a 1% agarose gel and purified using a BioRad Prep-A-Gene kit.

About 40 μl of TE buffer (pH 8.0) is added to 50 μl of vector along with 0.05 units of Calf Intestine Alkaline Phosphatase (BMB). The reaction is allowed to continue for 30 minutes at 37° C., then 10 μl of 500 mM EGTA is added as the temperature is shifted to 65° C. for 45 minutes. The vector is phenol/chloroform extracted, alcohol precipitated and resuspended in 20 μl of water.

About 5 μl of 0.1 μg/μl CAT GenBlock (PL Pharmacia HindIII CAT vector, Catalogue #27-4895-01), 5 μl of an equal volume mixture of 0.2 mM each of the 4 dNTPs (in 500 mM Tris pH 7.8, 50 mM MgCl$_2$, 100 mM 2-mercaptoethanol and 100 μg/ml nuclease free BSA) and 1 μl of Klenow (BRL) are mixed and left at 25° C. for 30 minutes. The mixture is heated at 70° C. for 5 minutes, then ethanol precipitated. The DNA is resuspended in 10 μl of 10 mM Tris (pH 7.6) and 2 μl ligation buffer (0.5M Tris, pH 7.6, 100 mM MgCl$_2$, 100 mM DTT and 500 μg/ml BSA), 2 μl (0.2 μg) phosphorylated BclI linkers (New England Biolabs), 1 μl bacteriophage T4 DNA ligase and 2 μl 10 mM ATP are added. Incubation occurs for 12 hours at 16° C., followed by 15 minutes at 68° C. Next, 20 μl of 10X BclI buffer, 150 μl of water and 20 μl of restriction enzyme BclI are added, then the mixture is incubated at 37° C. for 2 hours. After phenol/chloroform extraction and ethanol precipitation, the DNA is resuspended in 50 μl of H$_2$O and excess linkers are removed by passing to DNA through a Sepharose CL 4B Spin column.

The CAT gene is then ligated into the vector backbone by mixing 7 μl of vector, 1 μl of 10X ligase buffer, 1 μl of ligase and 1 μg of the CAT fragment for 12 hours at 16° C. The DNA is transformed into *E. coli* K12 AG1 competent cells (Stratagene) in substantial accordance with the previous Examples to form plasmid pGT-CAT.

Plasmid pGT-CAT is then transformed into 293 cells in substantial accordance with the teaching of previous Examples. Other vectors containing other promoters and transcriptions control units are also transformed into 293 cells and levels of transient expression as determined. Chloramphenicol acetyltransferase assays and human protein C ELISA tests are preferred as per Grinnell et al., 1987, *Biotechnology* 5:1189–1192; Grinnell et al., 1986, *Mol. Cell. Biol.* 6:3596–3605. Results are presented in Table I.

We claim:

1. A method for producing a eukaryotic polypeptide in a eukaryotic host cell, said eukaryotic host cell expressing an immediate-early gene product of a large DNA virus, said method comprising the steps of:

(a) transforming said host cell with a recombinant DNA vector comprising
      (i) a modified transcription control unit comprising
         (A) the P2 enhancer of BK virus spaced closely to the upstream regulatory element of the major late promoter of adenovirus
         (B) the adenovirus-2 major late promoter
         (C) a poly-GT element positioned to stimulate said promoter,
         (D) a DNA sequence containing the spliced tripartite leader sequence of adenovirus, wherein said modified transcription control unit comprises the sequence

AAGCTTTTCT CATTAAGGGA AGATTTCCCC

AGGCAGCTCT TTCAAGGGAT

CCTCGAGAAT TCACACACAC ACACACACAC

ACACACACAC ACACACACAC

ACACTAGAGG ATCCCTAAAA GGTCCATGAG

CTCCATGGAT TCTTCCCTGT

TAAGAACTTT ATCCATTTTT GCAAAAATTG

CAAAAGAATA GGGATTTCCC

CAAATAGTTT TGCTAGGCCT CAGAAAAAGC

CTCCACACCC TTACTACTTG

AGAGAAAGGG TGGAGGCAGA GGCGGCCTCG

GCCTCTTATA TATTATAAAA

AAAAAGGCCA CAGGGAGGAG CTGCTTACCC

ATGGAATGCA GCCAAACCAT

GACCTCAGGA AGGAAAGTGC ATGACTGGGC

AGCCAGCCAG TGGCAGTTAA

TAAGCAGCCA GACAGACATT TGCTTACCCA

TGGAATGCAG CCAAACCATG

ACCTCAGGAA GGAAAGTGCA TGACTGGGCA

GCCAGCCAGT GGCAGTTAAT

AAGCAGCAGC CAGACAGACA TGTTTTGCGA

GCCTAGTCGC CCTCTTCGGC

ATCAAGGAAG GTGATTGGTT TATAGGTGTA

GGCCACGTGA CCGGGTGTTC

CTGAAGGGGG GCTATAAAAG GGGGTGGGGG

CGCGTTCGTC CTCACTCTCT

TCCGCATCGC TGTCTGCGAG GGCCAGCTGT

TGGGCTCGCG GTTGAGGACA

AACTCTTCGC GGTCTTTCCA GTACTCTTGG

ATCGGAAACC CGTCGGCCTC

```
            -continued
CGAACGTACT CCGCCACCGA GGGACCTGAG

CGAGTCCGCA TCGACCGGAT

CGGAAAACCT CTCGAGAAAG GCGTCTAACC

AGTCACAGTC GCAAGCTT
``` and (ii) a DNA sequence encoding said eukaryotic polypeptide, said DNA sequence being positioned for expression of said eukaryotic polypeptide;

(b) culturing said cell of step (a) under conditions suitable for expressing said DNA sequence encoding said eukaryotic polypeptide, and (c) recovering said eukaryotic polypeptide from said cell culture.

2. The method of claim 1 wherein said eukaryotic host cell is an adenovirus transformed host cell.

3. The method of claim 1 wherein said eukaryotic polypeptide is human protein C.

4. The method of claim 2 wherein said eukaryotic host cell is selected from the group consisting of 293 and AV12-664 host cells.

5. The method of claim 4 wherein said eukaryotic host cell is a 293 cell.

6. The method of claim 5 wherein said eukaryotic polypeptide is human protein C.

7. A method for increasing the level of production of a eukaryotic polypeptide in a host cell, said method comprising:

(a) stably transforming a host cell with a vector which expresses said eukaryotic polypeptide, (b) transforming said stably transformed host cell of step (a) with a different vector, said vector comprising a gene encoding said eukaryotic polypeptide positioned such that transcription is driven by the GBMT transcription unit, (c) culturing said cell of step (b) under conditions suitable for expressing said gene encoding said eukaryotic polypeptide, and (d) recovering said eukaryotic polypeptide from said cell culture.

8. The method of claim 7 wherein said eukaryotic polypeptide is human protein C.

9. The method of claim 7 wherein said stably transformed host cell is 293/pLPC.

10. The method of claim 9 wherein said vector of step (b) is plasmid pGTC.

* * * * *